US012709609B2

(12) United States Patent
Wiedemann et al.

(10) Patent No.: US 12,709,609 B2
(45) Date of Patent: Aug. 18, 2026

(54) CRYSTALLINE FORM OF SELINEXOR

(71) Applicant: Karyopharm Therapeutics Inc., Newton, MA (US)

(72) Inventors: Sean Howard Wiedemann, Burlington, MA (US); Bojan Dragisic, Toronto (CA); Stephen Edmund Gottschling, Bolton (CA)

(73) Assignee: Karyopharm Therapeutics Inc., Newton, MA (US)

(*) Notice: Subject to any disclaimer, the term of this patent is extended or adjusted under 35 U.S.C. 154(b) by 490 days.

(21) Appl. No.: 18/032,949

(22) PCT Filed: Oct. 21, 2021

(86) PCT No.: PCT/US2021/055974

§ 371 (c)(1), (2) Date: Apr. 20, 2023

(87) PCT Pub. No.: WO2022/087218

PCT Pub. Date: Apr. 28, 2022

(65) Prior Publication Data

US 2023/0391754 A1 Dec. 7, 2023

Related U.S. Application Data

(60) Provisional application No. 63/094,666, filed on Oct. 21, 2020.

(51) Int. Cl.

*C07D 403/12* (2006.01)

*A61P 35/00* (2006.01)

(52) U.S. Cl.

CPC ............ *C07D 403/12* (2013.01); *A61P 35/00* (2018.01); *C07B 2200/13* (2013.01)

(58) Field of Classification Search

CPC .... C07D 403/12; A61P 35/00; C07B 2200/13

See application file for complete search history.

(56) References Cited

U.S. PATENT DOCUMENTS

| | | | |
|---|---|---|---|
| 5,153,201 | A | 10/1992 | Aono et al. |
| 5,817,677 | A | 10/1998 | Linz et al. |

(Continued)

FOREIGN PATENT DOCUMENTS

| | | | |
|---|---|---|---|
| CN | 101309912 | A | 11/2008 |
| CN | 101466687 | A | 6/2009 |

(Continued)

OTHER PUBLICATIONS

Balbach et al., Pharmaceutical evaluation of early development candidates: "The 100 mg-approach," International Journal of Pharmaceutics, 275:1-12 (2004).

(Continued)

*Primary Examiner* — Sarah Pihonak

*Assistant Examiner* — Jackson J Hernandez

(74) *Attorney, Agent, or Firm* — FOLEY HOAG LLP

(57) ABSTRACT

The invention relates to a crystalline form of the compound represented by Structural Formula 1, and pharmaceutical compositions comprising the crystalline form of the compound represented by Structural Formula 1 described herein. The crystalline form of the compound of Structural Formula 1 and compositions comprising the crystalline form of the compound represented by Structural Formula 1 provided herein, can be incorporated into pharmaceutical compositions, which can be used to treat various disorders. Also described herein are methods for preparing the crystalline form of the compound represented by Structural Formula 1.

23 Claims, 6 Drawing Sheets

(56) References Cited

U.S. PATENT DOCUMENTS

| | | | |
|---|---|---|---|
| 6,462,049 | B1 | 10/2002 | Ogura et al. |
| 7,342,115 | B2 | 3/2008 | Hutchison et al. |
| 7,667,041 | B2 | 2/2010 | Kimura et al. |
| 7,795,457 | B2 | 9/2010 | Fu et al. |
| 7,858,621 | B2 | 12/2010 | Kim et al. |
| 7,902,367 | B2 | 3/2011 | Nomura et al. |
| 8,273,738 | B2 | 9/2012 | Osakada et al. |
| 8,299,102 | B2 | 10/2012 | Strobel et al. |
| 8,304,438 | B2 | 11/2012 | Strobel et al. |
| 8,513,230 | B2 | 8/2013 | Shacham et al. |
| 8,598,168 | B2 | 12/2013 | Moradei et al. |
| 8,999,996 | B2 | 4/2015 | Sandanayaka et al. |
| 9,079,865 | B2 | 7/2015 | Sandanayaka et al. |
| 9,096,543 | B2 | 8/2015 | Sandanayaka et al. |
| 9,206,158 | B2 | 12/2015 | Sandanayaka et al. |
| 9,266,843 | B2 | 2/2016 | Sandanayaka et al. |
| 9,303,000 | B2 | 4/2016 | Sandanayaka et al. |
| 9,428,490 | B2 | 8/2016 | Sandanayaka et al. |
| 9,550,757 | B2 | 1/2017 | Shacham et al. |
| 9,585,874 | B2 | 3/2017 | Sandanayaka et al. |
| 9,714,226 | B2 | 7/2017 | Sandanayaka et al. |
| 9,738,624 | B2 | 8/2017 | Baloglu et al. |
| 9,828,373 | B2 | 11/2017 | Liu et al. |
| 9,861,614 | B2 | 1/2018 | Sandanayaka et al. |
| 10,058,535 | B2 | 8/2018 | Sandanayaka et al. |
| 10,173,987 | B2 | 1/2019 | Sandanayaka et al. |
| 10,202,366 | B2 | 2/2019 | Rashal et al. |
| 10,335,393 | B2 | 7/2019 | Sandanayaka et al. |
| 10,407,405 | B2 | 9/2019 | Baloglu et al. |
| 10,519,139 | B2 | 12/2019 | Austad et al. |
| 10,526,295 | B2 | 1/2020 | Baloglu |
| 10,544,108 | B2 | 1/2020 | Sandanayaka et al. |
| 10,709,706 | B2 | 7/2020 | Baloglu |
| 11,034,660 | B2 | 6/2021 | Sandanayaka et al. |
| 11,078,190 | B2 | 8/2021 | Austad et al. |
| 11,124,493 | B2 | 9/2021 | Baloglu et al. |
| 11,746,102 | B2 | 9/2023 | Austad et al. |
| 11,753,401 | B2 | 9/2023 | Austad et al. |
| 11,787,771 | B2 | 10/2023 | Sandanayaka et al. |
| 11,807,629 | B2 | 11/2023 | Austad et al. |
| 11,945,794 | B2 | 4/2024 | Baloglu et al. |
| 12,291,508 | B2 | 5/2025 | Sandanayaka et al. |
| 12,371,420 | B2 | 7/2025 | Austad et al. |
| 12,577,225 | B2 | 3/2026 | Baloglu et al. |
| 2002/0025539 | A1 | 2/2002 | Dellinger et al. |
| 2003/0018025 | A1 | 1/2003 | Thurkauf et al. |
| 2004/0092598 | A1 | 5/2004 | Watkins et al. |
| 2006/0004069 | A1 | 1/2006 | Momose et al. |
| 2009/0221586 | A1 | 9/2009 | Okada et al. |
| 2009/0298896 | A1 | 12/2009 | Sakuma et al. |
| 2010/0016272 | A1 | 1/2010 | Strobel et al. |
| 2010/0056569 | A1 | 3/2010 | Nan et al. |
| 2011/0009374 | A1 | 1/2011 | Keller |
| 2011/0275607 | A1 | 11/2011 | Shacham et al. |
| 2012/0258986 | A1 | 10/2012 | Sandanayaka et al. |
| 2013/0317031 | A1 | 11/2013 | Sandanayaka et al. |
| 2014/0155370 | A1 | 6/2014 | Shacham et al. |
| 2014/0235653 | A1 | 8/2014 | Sandanayaka et al. |
| 2014/0364408 | A1 | 12/2014 | Sandanayaka et al. |
| 2015/0018332 | A1 | 1/2015 | Sandanayaka et al. |
| 2015/0111893 | A1 | 4/2015 | Sandanayaka et al. |
| 2015/0274698 | A1 | 10/2015 | Sandanayaka et al. |
| 2016/0145246 | A1 | 5/2016 | Sandanayaka et al. |
| 2016/0152596 | A1 | 6/2016 | Baloglu et al. |
| 2016/0258931 | A1 | 9/2016 | Silva et al. |
| 2016/0304500 | A1 | 10/2016 | Rashal et al. |
| 2017/0137430 | A1 | 5/2017 | Sandanayaka et al. |
| 2017/0319551 | A1 | 11/2017 | Sandanayaka et al. |
| 2018/0052166 | A1 | 2/2018 | Villalba Gonzalez et al. |
| 2018/0155317 | A1 | 6/2018 | Baloglu et al. |
| 2019/0016690 | A1 | 1/2019 | Baloglu |
| 2019/0023693 | A1 | 1/2019 | Chennuru et al. |
| 2019/0160063 | A1 | 5/2019 | Baloglu |
| 2020/0087313 | A1 | 3/2020 | Sandanayaka et al. |
| 2020/0199099 | A1 | 6/2020 | Baloglu et al. |
| 2020/0283419 | A1 | 9/2020 | Austad et al. |
| 2020/0339521 | A1 | 10/2020 | Sandanayaka et al. |
| 2022/0056038 | A1 | 2/2022 | Sandanayaka et al. |
| 2022/0073478 | A1 | 3/2022 | Sandanayaka et al. |
| 2022/0135545 | A1 | 5/2022 | Austad et al. |
| 2022/0177445 | A1 | 6/2022 | Baloglu et al. |
| 2022/0178927 | A1 | 6/2022 | Califano et al. |
| 2023/0024251 | A1 | 1/2023 | Morant |
| 2023/0242516 | A1 | 8/2023 | Austad et al. |
| 2023/0391754 | A1 | 12/2023 | Wiedemann et al. |
| 2024/0208943 | A1 | 6/2024 | Austad et al. |
| 2024/0279188 | A1 | 8/2024 | Sandanayaka et al. |
| 2024/0376114 | A1 | 11/2024 | Sandanayaka et al. |
| 2025/0059158 | A1 | 2/2025 | Baloglu et al. |
| 2026/0062391 | A1 | 3/2026 | Sandanayaka et al. |

FOREIGN PATENT DOCUMENTS

| | | | |
|---|---|---|---|
| CN | 103002742 | A | 3/2013 |
| CN | 103874690 | B | 7/2016 |
| CN | 106831731 | A | 6/2017 |
| EP | 0069513 | A2 | 1/1983 |
| EP | 1939180 | A1 | 7/2008 |
| EP | 1992618 | A1 | 11/2008 |
| EP | 2003118 | A1 | 12/2008 |
| EP | 2 090 570 | A1 | 8/2009 |
| EP | 2736887 | A1 | 6/2014 |
| EP | 3808742 | A1 | 4/2021 |
| JP | S5841875 | A | 3/1983 |
| JP | S62103065 | A | 5/1987 |
| JP | H04211089 | A | 8/1992 |
| JP | H07118237 | A | 5/1995 |
| JP | H11263764 | A | 9/1999 |
| JP | 2003342262 | A | 12/2003 |
| JP | 2004509941 | A | 4/2004 |
| JP | 2004168768 | A | 6/2004 |
| JP | 2005508905 | A | 4/2005 |
| JP | 2005255683 | A | 9/2005 |
| JP | 2006504761 | A | 2/2006 |
| JP | 2007210929 | A | 8/2007 |
| JP | 2009203238 | A | 9/2009 |
| JP | 2009536615 | A | 10/2009 |
| JP | 2009544696 | A | 12/2009 |
| JP | 2010513341 | A | 4/2010 |
| JP | 2010519337 | A | 6/2010 |
| JP | 2015516434 | A | 6/2015 |
| JP | 2018012715 | A | 1/2018 |
| KR | 20050062645 | A | 6/2005 |
| WO | WO-1995/30783 | A1 | 11/1995 |
| WO | WO-1996/16040 | A1 | 5/1996 |
| WO | WO-1997/15567 | A1 | 5/1997 |
| WO | WO-1997/37996 | A1 | 10/1997 |
| WO | WO-1997/48696 | A1 | 12/1997 |
| WO | WO-1998/25893 | A1 | 6/1998 |
| WO | WO-1999/50264 | A1 | 10/1999 |
| WO | WO-2001/62756 | A1 | 8/2001 |
| WO | WO-2002/26696 | A1 | 4/2002 |
| WO | WO-2003/024448 | A2 | 3/2003 |
| WO | WO-2004/039365 | A1 | 5/2004 |
| WO | WO-2004/039764 | A1 | 5/2004 |
| WO | WO-2004/043925 | A2 | 5/2004 |
| WO | WO-2004/043951 | A1 | 5/2004 |
| WO | WO-2004/076418 | A1 | 9/2004 |
| WO | WO-2005/115990 | A1 | 12/2005 |
| WO | WO-2006/016637 | A1 | 2/2006 |
| WO | WO-2006/019020 | A1 | 2/2006 |
| WO | WO-2006/088246 | A1 | 8/2006 |
| WO | WO-2007/102580 | A1 | 9/2007 |
| WO | WO-2007/147336 | A1 | 12/2007 |
| WO | WO-2008/029825 | A1 | 3/2008 |
| WO | WO-2008/074413 | A2 | 6/2008 |
| WO | WO-2008/152097 | A1 | 12/2008 |
| WO | WO-2010/017545 | A2 | 2/2010 |
| WO | WO-2011/069039 | A1 | 6/2011 |
| WO | WO-2011/109799 | A1 | 9/2011 |
| WO | WO-2012/099807 | A1 | 7/2012 |
| WO | WO-2013/019548 | A1 | 2/2013 |
| WO | WO-2013/019561 | A1 | 2/2013 |
| WO | WO-2013/020024 | A2 | 2/2013 |

(56) References Cited

FOREIGN PATENT DOCUMENTS

| | | | |
|---|---|---|---|
| WO | WO-2013/170068 | A2 | 11/2013 |
| WO | WO-2014/144772 | A1 | 9/2014 |
| WO | WO-2014/152263 | A1 | 9/2014 |
| WO | WO-2014/205389 | A1 | 12/2014 |
| WO | WO-2014/205393 | A1 | 12/2014 |
| WO | WO-2016/025904 | A1 | 2/2016 |
| WO | WO-2017/040311 | A1 | 3/2017 |
| WO | WO-2017/117529 | A1 | 7/2017 |
| WO | WO-2017/117535 | A1 | 7/2017 |
| WO | WO-2017/118940 | A1 | 7/2017 |
| WO | WO-2018/098472 | A1 | 5/2018 |
| WO | WO-2018/129227 | A1 | 7/2018 |
| WO | WO-2020/198606 | A1 | 10/2020 |
| WO | WO-2022/087218 | A1 | 4/2022 |

OTHER PUBLICATIONS

Balsamini, "(E)-3-(2-(N-Phenylcarbamoyl)vinyl)pyrrole-2-carboxylic Acid Derivatives. A Novel Class of Glycine Site Antagonists", Journal of Medicinal Chemistry, 41(6):808-820 (1998).

Brekhov, Y. et al., "Cyanomethyltetrazoles II reactions of the methylene Fragment", Zhurnal organicheskoi Khimii, 28(9): 1921-1925 (1992).

Brittain, "Drugs in Pharmaceutical Sciences, v. 192. Polymorphism in Pharmaceutical Solids," CRC Press (2009).

Bryn et al., "Pharmaceutical Solids: A Strategic Approach to Regulatory Considerations," Pharma Res 12(7):945-954 (1995).

Buckler, R.T. et al., "Synthesis and Antiinflammatory Activity of Some 1,2,3- and 1,2,4-Triazolepropionic Acids", Journal of Medicinal Chemistry, 21(12): 1254-1260 (1978).

Burdeska et al., "Anil-Synthese. 23. Mitteilung. Ueber die Herstellung von Styryl- und Stilbenyl-Derivaten des Pyrimidins // Anil synthesis. Part 23. Preparation of styryl and stilbenyl derivatives of pyrimidines," Helv Chim Acta, 64(1): 113-152 (1981).

Cai, X., et al., "Inhibition of Thr-55 phosphorylation restores p53 nuclear localization and sensitizes cancer cells to DNA damage", Proc Nat Acad Sci, 105(44):16958-16963 (2008).

Caira, M.R., "Crystalline polymorphism of organic compounds". In: Weber, E., et al. Design of Organic Solids. Topics in Current Chemistry, vol. 198. pp. 163-208 (1998).

Cancer [online], [retrieved on Jul. 6, 2007] Retrieved from the Internet, URL: http://www.nlm.nih.gov/medlineplus/cancer.html (Year: 2007).

Cantu et al., "Using the Selective Inhibitor of Nuclear Export (SINE) Compound KPT-350 to Reduce Cortical Circuit Hyperexcitability and Interneuron Cell Loss in the Controlled Cortical Impact (CCI) Model of Traumatic Brain Injury (TBI) (I11.001)," Neurology, 86(16 Supplement):IT1.001 (2016).

CAS Registry No. 940775-13-3 (Jul. 2, 2007), 1 page.

Chemcats RN# 1035122-02-1; Publicly available on Jul. 12, 2009.

Chemcats RN# 1134927-58-4; Publicly available on Apr. 15, 2009.

Chemcats RN# 930886-49-0; Publicly available on Apr. 29, 2007.

Chemical Abstract Registry Nos. 1181485-58-4; 1100108-00-6 (2009).

Cheng et al., "XPO1 (CRM1) Inhibition Represses STAT3 Activation to Drive a Survivin-Dependent Oncogenic Switch in Triple-Negative Breast Cancer," Mol Cancer Ther 13(3):675-686 (2014).

Cooper et al., "Synthesis of Some 1,2,4-Triazoles and 1,2,4-Triazolines by Reaction of Oxamidrazone Condensation Products with Acetic Anhydride," Journal of Chemical Society Perkin Transactions l, 15: 1433-1437 (1975).

Cronshaw, J.M. et al., "The nuclear pore complex: disease associations and functional correlations", Trends Endocrin Metab. 15(1):34-39 (2004).

Daelemans, D. et al., "A synthetic HIV-1 Rev inhibitor interfering with the CRM1-mediated nuclear export", PNAS, 99(22):14440-14445 (2002).

Database PubChem Compound, Database Accession No. 33777540 (May 29, 2009), 3 pages.

Database PubChem Compound, Database Accession No. 33777561 (May 29, 2009), 3 pages.

Database PubChem Compound, Database Accession No. 33777585 (May 29, 2009), 3 pages.

Database PubChem Compound, Database Accession No. 66525271 (Oct. 24, 2012), 3 pages.

Database PubChem Compound, Database Accession No. 66525276 (Oct. 24. 2012), 3 pages.

Database PubChem Compound, Database Accession No. 72062355 (Dec. 2, 2007), 11 pages.

Davis, J.R. et al., "Controlling protein compartmentalization to overcome disease" Pharmaceut Res., 24(1):17-27 (2007).

Dorwald, "Side Reactions in Organic Synthesis: A Guide to Successful Synthesis Design," Wiley-VCH Verlag GmbH & Co. KGaA, Weinheim (2005).

Etchin et al., "KPT-330 inhibitor of CRM1 (XPO1)-mediated nuclear export has selective anti-leukemic activity in preclinical models of T-cell acute lymphoblastic leukaemia and acute myeloid leukaemia," British Journal of Haematology, 161:117-127 (2013).

Extended European Search Report for EP Application No. 17189480.1 dated May 16, 2018.

Extended European Search Report for EP Application No. 22176543.1 dated Oct. 12, 2022.

Extended European Search Report for EP Application No. 23162715.9 dated Aug. 9, 2023.

Extended European Search Report for EP Application No. EP 18202641 mailed Feb. 15, 2019.

Extended European Search Report issued by the European Patent Office in corresponding European Application No. 18164757.0 issued Aug. 8, 2018.

Extended Search Report for EP Application No. 11751491.9, "Nuclear Transport Modulators and Uses Thereof", Date of Completion of the Search: Dec. 17, 2013.

Extended Search Report for EP Application No. 12736172.3, "Olefin Containing Nuclear Transport Modulators and Uses Thereof", Date of Completion of the Search: May 8, 2014, 3 pages.

Falini, B. et al., "Both carboxy-terminus NES motif and mutated tryptophan(s) are crucial for aberrant nuclear export of nucleophosmin leukemic mutants in NPMc+ AML", Blood, 107(11):4514-4523 (2013).

Freundt, E.C. et al., "Molecular Determinants for Subcellular Localization of the Severe Acute Respiratory Syndrome Coronavirus Open Reading Frame 3b Protein", Journal of Virology, 83(13):6631-6640 (2009).

Ghildyal, R. et al., "The Respiratory Syncytial Virus Matrix Protein Possesses a Crm1-Mediated Nuclear Export Mechanism", Journal of Virology, 83(11):5353-5362 (2009).

Ghosh, C.C. et al., "Analysis of nucleocytoplasmic shuttling of NF kappa B proteins in human leukocytes", Methods Mol. Biol. 457:279-92 (2008).

Gilmore C.J. X-ray diffraction. In: Storey R.A., Ymén I., editors. Solid state characterization of pharmaceuticals. Chichester: Blackwell Publishing; p. 35-70 (2011).

Golub, T.R. et al., "Molecular Classification of Cancer: Class Discovery and Class Prediction by Gene Expression Monitoring", Science, 286: 531-537 (1999).

Gravina et al., "XPO1/CRM1-Selective inhibitors of nuclear export (SINE) reduce tumor spreading and improve overall survival in preclinical models of prostate cancer (PCa)," Journal of Hematology & Oncology, 7(46): (2014).

Gupta, N. et. al., "Retinal tau pathology in human glaucomas" Can J Ophthalmol. 43(1):53-60 (2008).

Haines et al., "Selective Inhibitors of Nuclear Export Avert Progression in Preclinical Models of Inflammatory Demyelination," Nature Neuroscience, 18(4): 511-520 (2015).

Hilliard et al., "The anti-inflammatory prostaglandin 15-Deoxy-Δ12,14 PGJ2 inhibits CRM1-dependent nuclear protein export," Journal of Biological Chemistry, 285(29): 22202-22210 (2010).

Hoffman et al., "Synthesis of Vinyl-Functionalized Oxazoles by Olefin Cross-Metathesis", J. Org. Chem. 73: 2400-2403 (2008).

Hoshino, I. et al., "Combined effects of p53 gene therapy and leptomycin B in human esophageal squamous cell carcinoma", Oncology, 75:113-119 (2008).

(56) References Cited

OTHER PUBLICATIONS

Huff, J., "HIV Protease: A Novel Chemotherapeutic Target for AIDS", Journal of Medicinal Chemistry, 34(8): 2305-2314 (1991).
International Preliminary Report on Patentability for International Application No. PCT/US2011/027328, "Nuclear Transport Modulators and Uses Thereof" dated Sep. 11, 2012.
International Preliminary Report on Patentability for International Application No. PCT/US2012/021406, "Olefin Containing Nuclear Transport Modulators and Uses Thereof" dated Jul. 17, 2013.
International Preliminary Report on Patentability for International Application No. PCT/US2014/029322 dated Sep. 15, 2015.
International Preliminary Report on Patentability for International Application No. PCT/US2014/043479, dated Dec. 22, 2015.
International Preliminary Report on Patentability for International Application No. PCT/US2014/043484, dated Dec. 22, 2015.
International Preliminary Report on Patentability for International Application No. PCT/US2015/045395 mailed Feb. 21, 2017.
International Preliminary Report on Patentability for International Application No. PCT/US2016/069492 issued Jul. 3, 2018.
International Preliminary Report on Patentability for International Application No. PCT/US2016/069508 issued Jul. 3, 2018.
International Preliminary Report on Patentability for International Application No. PCT/US2017/063439 mailed May 28, 2019.
International Preliminary Report on Patentability for International Application No. PCT/US2012/048319, "Hydrazide Containing Nuclear Transport Modulators and Uses Thereof"; Date of Issuance of the Report: Feb. 4, 2014.
International Preliminary Report on Patentability for International Application No. PCT/US2012/048368, Nuclear Transport "Modulators and Uses Thereof"; Date of Issuance of the Report: Feb. 4, 2014.
International Preliminary Report on Patentability for International Application No. PCT/US2013/040404, "Nuclear Transport Modulators and Uses Thereof"; Date of Issuance of the Report: Nov. 11, 2014.
International Search Report and the Written Opinion of the International Searching Authority for International Application No. PCT/US2012/021406, "Olefin-Containing Nuclear Transport Modulators and Uses Thereof" dated Apr. 30, 2012.
International Search Report and the Written Opinion of the International Searching Authority for International Application No. PCT/US2012/049470, "Maleimide Compounds and Methods of Treatment," dated Feb. 13, 2013.
International Search Report and the Written Opinion of the International Searching Authority for International Application No. PCT/US2013/040404, "Nuclear Transport Modulators and Uses Thereof"; Date of Mailing: Nov. 18, 2013.
International Search Report and the Written Opinion of the International Searching Authority, or the Declaration for International Application No. PCT/US2014/027136 "Exo Olefin-Containing Nuclear Transport Modulators and Uses Thereof"; Date of Mailing: Jul. 11, 2014.
International Search Report and the Written Opinion of the International Searching Authority, or the Declaration for International Application No. PCT/US2014/029322 "Methods of Promoting Wound Healing Using CRM1 Inhibitors"; Date of Mailing: May 28, 2014.
International Search Report and the Written Opinion of the International Searching Authority, or the Declaration for International Application No. PCT/US2014/043479 "Nuclear Transport Modulators and Uses Thereof"; Date of Mailing: Sep. 17, 2014.
International Search Report and the Written Opinion of the International Searching Authority, or the Declaration for International Application No. PCT/US2014/043484 "Nuclear Transport Modulators and Uses Thereof"; Date of Mailing: Sep. 2, 2014.
International Search Report and Written Opinion for International Application No. PCT/US2015/045395 mailed Jan. 12, 2016.
International Search Report and Written Opinion for International Application No. PCT/US2016/069492 mailed Feb. 16, 2017.
International Search Report and Written Opinion for International Application No. PCT/US2016/069508 mailed May 23, 2017.
International Search Report and Written Opinion for International Application No. PCT/US2017/063439 mailed Feb. 2, 2018.
International Search Report and Written Opinion for International Application No. PCT/US2021/055974 mailed Jan. 4, 2022.
International Search Report for International Application No. PCT/US2011/027328, "Nuclear Transport Modulators and Uses Thereof" dated Apr. 29, 2011.
International Search Report for International Application No. PCT/US2012/048319, "Hydrazide Containing Nuclear Transport Modulators and Uses Thereof" date of mailing: Nov. 9, 2012.
International Search Report for International Application No. PCT/US2012/048368, "Nuclear Transport Modulators and Uses Thereof" date of mailing Sep. 21, 2012.
Jiang et al., "Palladium-Catalyzed Alkenylation of 1,2,3-Trizoles with Terminal Conjugated Alkenes by Direct C—H Bond Functionalization," Eur J Org Chem, 7:1227-30 (2010).
Karyagin, A. Yu., "Reagents for addressed modification of biopolymers 11. The synthesis of N Im-2,4-dinitrophenyl derivatives of histidine and urocanic and imidazolylacetic acids for anchoring imidazole residues to oligonucleotides," Russian Chemical Bulletin, 2000, 49(3):540-5.
Karyopharm Therapeutics, "Karyopharm Presents Data Demonstrating the Potential of Nuclear Export Protein Exportin 1 (XPO1) Inhibition in the Treatment of Traumatic Brain Injury," Apr. 20, 2016, Retrieved from the Internet: http://investors.karyopharm.com/static-files/577eb861-4183-463a-9a5b-d0f1def1629d [retrieved on Jan. 25, 2018].
Kau, T.R. et al., "A chemical genetic screen identifies inhibitors of regulated nuclear export of a Forkhead transcription factor in PTEN-deficient tumor cells", Cancer Cell, pp. 4(6): 463-476 (2003).
Kaur et al., "Tyrphostin Induced Growth Inhibition: Correlation with Effect on p210bcr-abl Autokinase Activity in K562 Chronic Myelogenous Leukemia," Anti-Cancer Drugs, 5(2): 213-222 (1994).
Ke, S.-Y. et al., "Research Advance of Acylhydrazine Derivatives with Biological Activities", Chinese Journal of Organic Chemistry 30(12):1820-1830 (2010).
Lain, S. et al., "Accumulating active p53 in the nucleus by inhibition of nuclear export: a novel strategy to promote the p53 tumor suppressor function", Exp Cell Res. 253: 315-324 (1999).
Lain, S. et al., "An inhibitor of nuclear export activates the p53 response and induces the localization of HDM2 and p53 to U1A-positive nuclear bodies associated with the PODs", Exp Cell Res. 248:457-472 (1999).
Lala, P.K. et al., "Role of nitric oxide in tumor progression: Lessons from experimental tumors", Cancer and Metastasis Reviews, 17: 91-106 (1998).
Lapalombella, R. et al., "Selective Inhibitors of nuclear exports show that CRM1/XPO1 is a target in chronic lymphocytic leukemia", Blood, 120(23): 4621-4634 (2012).
Li, A. et al., "Upregulation of CRM1 Relates to Neuronal Apoptosis after Traumatic Brain Injury in Adult Rats", J Mol Neurosci, 51(1):208-218 (2013).
Maekawa et al., "Efficient Formation of a Triazole Ring via Novel Ring-Opening Reaction of (z)-2-Methyl-4-arylmethylene-5(4H)-Oxazolones with Hydrazides," Heterocycles, 75(12): 2959-2971 (2008).
Maga et al., "Pharmacophore modeling and molecular docking led to the discovery of inhibitors of human immunodeficiency virus-1 replication targeting the human cellular aspartic acid-glutamic acid-alanine-aspartic acid box polypeptide 3," J Med Chem, 51(21):6635-6638 (2008).
Marelli et al., "Tumor targeting via integrin ligands," Frontiers in Oncology, 3(222):1-12 (2013).
Miskolci et al., "TNFα release from peripheral blood leukocytes depends on a CRM1-mediated nuclear export," Biochemical and Biophysical Research Communications, 351:354-360 (2006).
Modzelewska-Banachiewicz, B. et al., "Synthesis and biological activity of (Z) and (E) isomers of 3-(3,4-diaryl-1,2,4-triazole-5-yl)prop-2-enoic acid" Monatsh Chem., 140:439-444 (2009).
Modzelewska-Banachiewicz, B. et al., "Synthesis and biological activity of new derivatives of 3-(3,4-diaryl-1,2,4-triazole-5-yl)propenoic acid" European Journal of Medicinal Chemistry, 39:873-877 (2004).

(56) References Cited

OTHER PUBLICATIONS

Monecke, T. et al., "Crystal Structure of the Nuclear Export Receptor CRM1 in Complex with Snurportin1 and RanGTP", Science, 324:1087-1091 (2009).
Morales et al., Mechanical Particle-Size Reduction Techniques. In: Williams III, R., Watts, A., Miller, D. (eds) Formulating Poorly Water Soluble Drugs. AAPS Advances in the Pharmaceutical Sciences Series, vol. 3. Springer, New York, NY (2012).
Morissette et al., "High-throughput crystallization: polymorphs, salts, co-crystals and solvates of pharmaceutical solids," Adv Drug Deliv Rev, 56(3):275-300 (2004).
Muller, P.A.J. et al., "Nuclear-Cytosolic Transport of COMMD1 Regulates NF-κB and HIF-1 Activity", Traffic, 10:514-527 (2009).
Mutka et al., "Identification of Nuclear Export Inhibitors with Potent Anticancer Activity in Vivo," Cancer Research, 69(2): 510-517 (2009).
Mutka, S. et al., "Nuclear export inhibitors (NEIs) as novel cancer therapeutics", 98th AACr Ann. Mtg., 2 pgs (Apr. 14-18, 2007) (Poster).
Nagase, The Practice of Medicinal Chemistry, Chapter 13. Conversion of Molecules Based on Equivalent Substitution, vol. 1, Technomics Inc., 1998, 253.
Nair, V., "Thermally induced skeletal rearrangement in a triazepine," J Heterocyclic Chem, 12(1):183-4 (1975).
Nakahara, J. et al., "Abnormal expression of TIP30 and arrested nucleocytoplasmic transport within oligodendrocyte precursor cells in multiple sclerosis", Journal of Clinical Investigation, 119(1):169-181 (2009).
Nautiyal et al., "Distinct functions for RIP140 in development, inflammation, and metabolism," Trends in Endocrinology and Metabolism, 24(9):451-459 (2013).
Noske, A., et al., "Expression of the Nuclear Export Protein Chromosomal Region Maintenance/Exportin 1/Xpo1 Is a Prognostic Factor in Human Ovarian Cancer", Cancer, 112(8):1733-1743 (2008).
Orsted et al., "Basic principles of wound healing," Wound Care Canada, 9(2): 4-12 (2011).
Patani, G.A., et al., "Bioisosterism: A Rational Approach in Drug Design", Chem Rev, 96:3147-3176 (1996).
Procopiou et al., "Inhibitors of Cholesterol Biosynthesis. 2. 3,5-Dihydroxy-7-(N-pyrrolyl)-6-heptenoates, a Novel Series of HMG-COA Reductase Inhibitors," J Med Chem, 36(23): 3658-3662 (1993).
Quan, M.L. et al., "Design and Synthesis of Isoxazoline Derivatives as Factor Xa Inhibitors", J. Med. Chem. 42: 2760-2773 (1999).
Rawlinson, S.M. et al., "CRM1-mediated Nuclear Export of Dengue Virus RNA Polymerase NS5 Modulates Interleukin-8 Induction and Virus Production", Journal of Biological Chemistry, 284(23):15589-15597 (2009).
Registry(STN) [online] Nov. 25, 1993, CAS Registration No. 151446-45-6.
Registry(STN)[online], Jan. 23, 2008, CAS registered No. 1000508-38-2, 1 page.
Sakamoto et al., "Studies on Pyrimidine Derivatives. XXV. Reaction of Pyrimidinyl Aldehydes and Ketones with Wittig Reagents," Chem Pharm Bull, 30(2): 610-614 (1982).
Sanchez, V. et al., "Nuclear Export of the Human Cytomegalovirus Tegument Protein pp65 Requires Cyclin-Dependent Kinase Activity and the Crm1 Exporter", Journal of Virology, 81(21):11730-11736 (2007).
Shasheva, "Reactions of Hydroxyphenyl-Substituted 1,2,4-Triazoles with Electrophilic Reagents", Russian Journal of General Chemistry, 79(10): 2234-2243 (2009).
Singhal et al., "Drug Polymorphism and Dosage Form Design: A practical perspective," Advanced Drug Delivery Reviews, 56:335-347 (2004).
Sorokin, A.V. et al., "Nucleocytoplasmic Transport of Proteins", Biochemistry Moscow, 72(13):1439-1457 (2007).
Sun Q., et al., "Nuclear export inhibition through covalent conjugation and hydrolysis of Leptomycin B by CRM1", Proc Nat Acad Sci, 110(4): 1303-1308 (2013).
Tai et al., "CRM1 inhibition induces tumor cell cytotoxicity and impairs osteoclastogenesis in multiple myeloma: molecular mechanisms and therapeutic implications," Leukemia, 28:155-165 (2014).
Tamir et al., "KPT-350, a Selective Inhibitor of Nuclear Export (SINE) Compound, Shows Efficacy in the Mouse Pilocapine Model of Temporal Lobe Epilepsy," Journal of Neurological Sciences, 381 (Suppl): 87-88 (2017).
Terry, L.J. et al., "Crossing the Nuclear Envelope: Hierarchical Regulation of Nucleocytoplasmic Transport", Science, 318:1412-1416 (2007).
Van der Watt, P.J. et al., "The Karyopherin proteins, Crm1 and Karyopherin β1, are overexpressed in cervical cancer and are critical for cancer cell survival and proliferation", Int. J. Cancer, 124:1829-1840 (2009).
Van Neck et al., "Inhibition of the CRM1-mediated nucleocytoplasmic transport by N-azolylacrylates: Structure-activity relationship and mechanism of action", Bioorganic & Medicinal Chemistry 16:9487-9497 (2008).
Walsh, Jr., M.D., et al., "Exportin 1 Inhibition Attenuates Nuclear Factor-kappaB-Dependent Gene Expression", Shock, 29(2):160-166 (2008).
Wang et al., "Mathematical modeling in cancer drug discovery," Drug Discovery Today, 19(2):145-150 (2014).
Williams, P., et al., "Characterization of a CRM1-Dependent Nuclear Export Signal in the C Terminus of Herpes Simplex Virus Type 1 Tegument Protein UL47", Journal of Virology, 82(21):10946-10952 (2008).
Written Opinion of the International Searching Authority for International Application No. PCT/US2011/027328, "Nuclear Transport Modulators and Uses Thereof" dated Apr. 29, 2011, 8 pages.
Written Opinion of the International Searching Authority for International Application No. PCT/US2012/048319, "Hydrazide Containing Nuclear Transport Modulators and Uses Thereof" dated Nov. 9, 2012, 9 pages.
Written Opinion of the International Searching Authority for International Application No. PCT/US2012/048368, "Nuclear Transport Modulators and Uses Thereof" dated Sep. 21, 2012, 11 pages.
Wu et al., Application of temperature cycling for crystal quality control during crystallization, CrystEngComm, 18(13): 2222-2238 (2016).
Yao, Y., et al., "The expression of CRM1 is associated with prognosis in human osteosarcoma", Oncology Reports, 21:229-235 (2009).
Yonemochi, "Physicochemical Properties for Amorphous Pharmaceuticals and their Stability," Cryobiol and Cryotechnol 51(1):25-30 (2005).
Zheng et al., "KPT-330 inhibitor of XPO1-mediated nuclear export has anti-proliferative activity in hepatocellular carcinoma," Cancer Chemother Pharmacol, 74:487-495 (2014).
Zimmerman, T.L. et al., "Nuclear Export of Retinoid X Receptor α in Response to Interleukin-1β-mediated Cell Signaling Roles for JNK and Ser260", Journal of Biological Chemistry, 281(22):15434-15440 (2006).
Abarbri et al., "Efficient synthesis of conjugated (2E)-or (2Z)-n-4-ynoic acids and (2E, 4E)-or (2Z, 4E)-dienoic acids via palladium-catalysed cross coupling", Synthesis 1996, issue 1, pp. 82-86.
Adamik et al., "EZH2 or HDAC1 Inhibition Reverses Multiple Myeloma-Induced Epigenetic Suppression of Osteoblast Differentiation," Molecular Cancer Research 15.4 (2017): 405-417.
Alvarez et al., "Network-based inference of protein activity helps functionalize the genetic landscape of cancer," Nature Genetics 48.8 (2016): 838-847.
Balkhi et al., "Proteomics of acute myeloid leukaemia: cytogenetic risk groups differ specifically in their proteome, interactome and post translational protein modifications" Oncogene 25:7041-7058 (2006).
Bell, "The TOLL of inflammation in multiple myeloma," Cancer Biology & Therapy 11.1 (2011):68-70.
Chari et al., "Results of the pivotal Storm study (Part 2) in penta-refractory multiple myeloma (MM): Deep and durable responses

(56) References Cited

OTHER PUBLICATIONS with oral selinexor plus low dose dexamethasone in patients with penta-refractory MM," Blood: 60th Annual Meeting of the America-Society-of-Hematology, 132(1):598 (2018).
Chen et al., "Safety and efficacy of selinexor in relapsed or refractory multiple myeloma and waldenstrom macroglobulinemia," Blood, 131(8):855-863 (2018).
De Campos et al., "Integrative analysis of FISH, transcriptomics and mutational status predicts responsiveness to novel agents in multiple myeloma," Blood, 134(1):574 (2019).
Hyatt et al., "Examining Telomere Dysfunction in Multiple Myeloma," PHD Thesis Dissertation—Cardiff University School of Medicine. 2017.
International Search Report and Written Opinion for International Application No. PCT/US20/25275 dated Aug. 31, 2020.
Invitation to Pay Additional Fees for International Application No. PCT/US20/25275 dated Jul. 8, 2020.
Podar et al., "Current and developing synthetic pharmacotherapy for treating relapsed/refractory multiple myeloma," Expert Opinion on Pharmacotherapy 18.11 (2017):1061-1079.
Richardson et al., "Panorama 2: panobinostat in combination with bortezomib and dexamethasone in patients with relapsed and bortezomib-refractory myeloma," Blood 122.14(2013): 2331-2337.
Rosebeck et al., "Effects of inhibition of XP01/CRM1-dependent nuclear export by selinexor (KPT-330), alone and in combination with carfilzomib (CFZ), on apoptosis and autophagy in multiple myeloma (MM)," Blood, 122(21):279 (2013).
Schmidt et al., "Genome-wide studies in multiple myeloma identify XP01/CRM1 as a critical target validated using the selective nuclear export inhibitor KPT-276," Leukemia, 27(12):2357-2365 (2013).
Silva et al., "An Ex Vivo Platform for the Prediction of Clinical Response in Multiple Myeloma," Cancer Research 77(12) (2017):3336-3351.
Sun et al., "Inhibiting cancer cell hallmark features through nuclear export inhibition." Signal Transduction and Targeted Therapy 1.1 (2016): 1-10.
Talmadge et al., "History of myeloid-derived suppressor cells," Nature Reviews Cancer 13 (2013): 739-752.
Tominaga et al., "Studies on Positive Inotropic Agents. I. Synthesis of 3,4-Dihydro-6-[4-(3,4-dimethoxybenzoyl)-1-piperazinyl]-2(1H)-quinolinone and Related Compounds", Chem. Pharm. Bull. 32(6): 2100-2110 (1984).
Turki et al., "Transfer Learning Approaches to Improve Drug Sensitivity Prediction in Multiple Myeloma Patients," IEEE Access 5 (2017): 7381-7393.
Vij et al., "Clinical Validation of Treatment Response Predictions Using a Genomics Driven Computational Biology Modelling Multiple Myeloma Algorithm." Blood, vol. 132, No. S1, pp. 1893 (2018).
Vogl et al., "Selinexor and Low Dose Dexamethasone (Sd) in Patients with Lenalidomide, Pomalidomide, Bortezomib, Carfilzomib and AntiCD38 Ab Refractory Multiple Myeloma (MM): STORM Study." Blood, vol. 128, No. 22, pp. 491. (2016).
Weaver et al., "Multiple Myeloma Genomics: A Systematic Review," Seminars in Oncology Nursing 33.3 (2017): 237-253.
Zhan et al., "The molecular classification of multiple myeloma" Blood 108(6):2020-2028 (2006).

CRYSTALLINE FORM OF SELINEXOR

RELATED APPLICATIONS

This application is the U.S. National Stage of International Application No. PCT/US2021/055974, filed Oct. 21, 2021, which designates the U.S., published in English, and claims the benefit of U.S. Provisional Application No. 63/094,666, filed on Oct. 21, 2020. The entire teachings of the above applications are incorporated herein by reference.

BACKGROUND OF THE INVENTION

Cells from most major human solid and hematologic malignancies exhibit abnormal cellular localization of a variety of oncogenic proteins, tumor suppressor proteins, and cell cycle regulators (Cronshaw et al, 2004, Falini et al 2006). For example, certain abnormalities lead to localization of important cellular regulator molecules in the cytoplasm rather than in the nucleus. Restoration of appropriate nuclear localization of cellular regulators can normalize some properties of neoplastic cells can restore sensitivity of cancer cells to DNA damaging agents and can lead to regression of established tumors.

Specific proteins and RNAs are carried into and out of the nucleus by specialized transport molecules, which are classified as importins if they transport molecules into the nucleus, and exportins if they transport molecules out of the nucleus. Proteins that are transported into or out of the nucleus contain nuclear import/localization (NLS) or export (NES) sequences that allow them to interact with the relevant transporters. One of major exportins is Chromosomal Region Maintenance 1 (CRM1), which is also called exportin-1 or Xpo1.

U.S. Pat. No. 9,079,865 describes compounds having inhibitory activity against CRM1, useful in the treatment of disorders associated with CRM1 activity, such as cancer. (Z)-3-(3-(3,5-bis(trifluoromethyl)phenyl)-1H-1,2,4-triazol-1-yl)-N'-(pyrazin-2-yl) acrylohydrazide (also referred to as Selinexor) is one of the compounds disclosed in U.S. Pat. No. 9,079,865, which is incorporated herein by reference in its entirety. Selinexor has the chemical structure shown in Structural Formula 1:

(1)

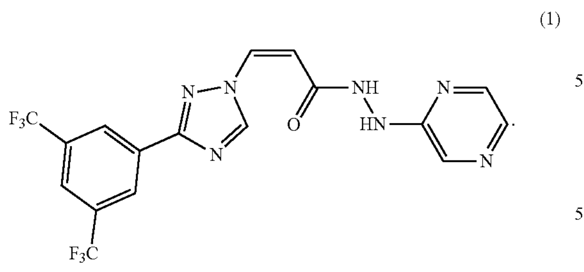

U.S. Pat. No. 10,519,139 describes crystalline forms of the compound represented by Structural Formula I, and compositions comprising crystalline forms of the compound represented by Structural Formula I. The crystalline forms of the compound of Structural Formula I describes in this publication, in particular, crystalline Form A, can be incorporated into pharmaceutical compositions, which can be used to treat various disorders associated with CRM1 activity, including cancer.

The solid form of a compound can be important in the formulation of pharmaceutical compositions. For example, different crystalline forms of a compound can have different physical properties (e.g., stability, dissolution rate, density, etc.) relating to their suitability for use in pharmaceutical compositions.

There is a need for crystalline forms of the compound of Structural Formula 1 that are thermodynamically stable and suitable for use in pharmaceutical compositions (e.g., are readily dissolvable, exhibit low hygroscopicity, good flow properties and/or good chemical and thermal stability). There is a further need for crystalline forms of the compound of Structural Formula 1 having physical properties that enable the manufacture of the compound of Structural Formula 1 and its pharmaceutical compositions in high yield and high purity with long shelflife.

SUMMARY OF THE INVENTION

The present invention relates to a crystalline form of the compound represented by Structural Formula 1, designated crystalline Form ZL, and compositions comprising the crystalline form.

In one embodiment, the present invention is a crystalline form of the compound represented by Structural Formula 1:

(1)

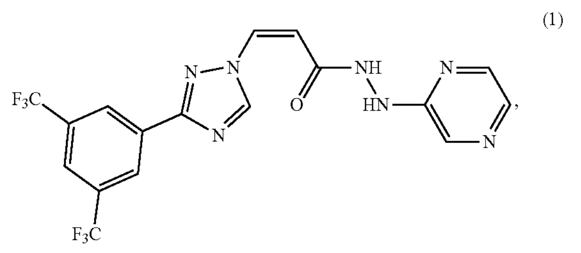 [SMILES: O=C(/C=C\n1cnc(-c2cc(C(F)(F)F)cc(C(F)(F)F)c2)n1)NNc1cnccn1]

wherein the crystalline form is Form ZL characterized by X-ray powder diffraction peaks at 2θ angles 18.75°, 20.16°, 21.37°, and 23.49°.

In another embodiment, the present invention is a method of preparing crystalline form of the compound represented by Structural Formula 1:

(1)

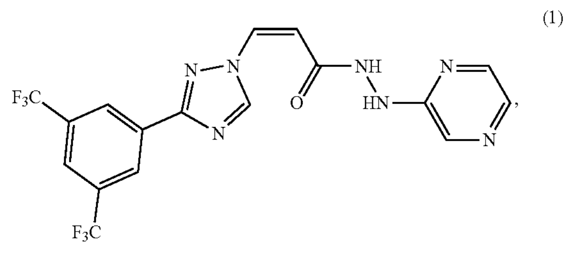 [SMILES: O=C(/C=C\n1cnc(-c2cc(C(F)(F)F)cc(C(F)(F)F)c2)n1)NNc1cnccn1]

wherein the crystalline form is Form ZL characterized by x-ray powder diffraction peaks at 2θ angles 18.75°, 20.16°, 21.37°, and 23.49°, the method comprising: combining crystalline Form A of the compound represented by Structural Formula 1 with a solvent, thereby generating a mixture; thermally cycling the mixture at least once; and isolating the solid particles of crystalline Form ZL, wherein thermally cycling the mixture comprises: heating the mixture to a first temperature over a first period of time; and cooling the mixture to a second temperature over a second period of time.

In another embodiment, the present invention relates to a method for treating or preventing a CRM1-associated disease or disorder, the method comprising administering to a subject in need thereof a therapeutically or prophylactically effective amount of the crystalline form of the compound represented by Structural Formula (I), as described herein.

In another embodiment, the present invention relates to a method for promoting wound healing in a subject in need thereof, comprising administering to the subject in need thereof a therapeutically effective amount of the crystalline form of the compound represented by Structural Formula (I) or a pharmaceutical composition, as described herein.

BRIEF DESCRIPTION OF THE DRAWINGS

The foregoing will be apparent from the following more particular description of example embodiments of the invention.

DETAILED DESCRIPTION OF THE INVENTION

Figure 1:
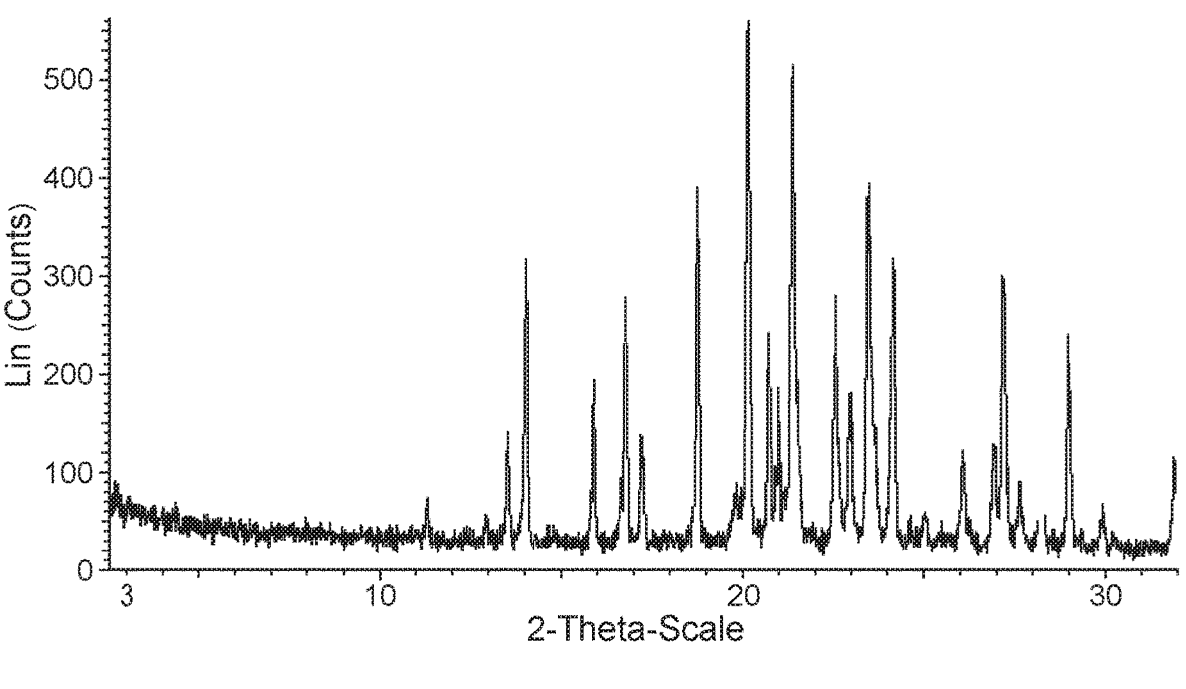
FIG. 1 is an x-ray powder diffraction (XPRD) pattern of the crystalline Form ZL of the compound represented by Structural Formula 1 (Sample was ground prior to analysis and transmittance mode use for analysis).

A description of example embodiments of the invention follows.

Crystalline Forms of the Compound of Structural Formula 1

It is to be understood that the term "about", when referring to a numerical value for temperature, means that the numerical value has a range±5° C. of the recited numerical value, unless specified otherwise. For example, when a described embodiment or a claim recites a temperature of "about 20° C.", this is to be understood to mean 20° C.±5° C., that is, a temperature from 15° C. to 25° C.

It is to be understood that the term "about", when referring to a numerical value for time, means that the numerical value has a range±5 minutes of the recited numerical value, unless specified otherwise. For example, when a described embodiment or a claim recites a period of time of "about 60 minutes", this is to be understood to mean 60 minutes±5 minutes, that is, a period of time from 55 minutes to 65 minutes.

"Alcohol-to-water volume ratio", as used herein, refers to the ratio of the volume of alcohol to the volume of water in the solvent. Alcohol-to-water volume ratio is expressed as x/(100-x), where "x" is the volume percent of alcohol in the solvent and "(100-x)" is the volume percent of water in the solvent. For example, when a described embodiment or a claim recites an alcohol-to water volume ratio of 70/30, this is to be understood that the volume percent of alcohol is 70%, while the volume percent of water is 30%.

It is to be understood that the term "about", when referring to a numerical value for an alcohol-to-water volume ratio, means that the numerical value for x has a range±5% of the recited numerical value, unless specified otherwise. For example, when a described embodiment or a claim recites an alcohol-to-water volume ratio of "about 70/30", this is to be understood to mean an alcohol-to-water volume ratio from 75/25 to 65/35.

Provided herein is a crystalline form of the compound of Structural Formula 1, designated crystalline Form ZL.

"Crystalline" or "crystal," as used herein, refers to a homogeneous solid formed by a repeating, three-dimensional pattern of atoms, ions or molecules (e.g., an anhydrous molecule or a salt thereof, solvate thereof, or combination of the foregoing) having fixed distances between constituent parts. The unit cell is the simplest repeating unit in this pattern.

The crystalline forms provided herein can be identified on the basis of characteristic peaks in an x-ray powder diffraction (XRPD) analysis. XRPD is a scientific technique that measures the x-rays, neutrons or electrons scattered by a powder or microcrystalline material as a function of scattering angle. XRPD can be used to identify and characterize crystalline solids, as the diffraction pattern produced by a particular solid is typically distinctive to that solid and can be used as a "fingerprint" to identify that solid. For example, an XRPD pattern or diffractogram (e.g., a pattern or diffractogram produced by a sample, such as an unknown sample) that is substantially in accordance with a reference XRPD pattern or diffractogram can be used to determine the identity between the sample material and the reference material. Both the position and the relative intensity of the peaks in an XRPD diffractogram are indicative of the particular phase and identity of a material.

A crystalline form provided herein can be a sole crystalline form or can comprise a mixture of two or more different crystalline forms. For example, in some embodiments, crystalline Form ZL of the compound represented by Structural Formula 1 is provided as a sole crystalline form. Alternatively, in other embodiments, a crystalline form can comprise a mixture of two or more crystalline forms of the compound represented by Structural Formula 1, e.g., a mixture of crystalline Form ZL with one or more of crystalline forms of the compound represented by Structural Formula 1, such as crystalline Forms A, B, C, and D, which are disclosed in the U.S. Pat. No. 10,519,139. U.S. Pat. No. 10,519,139 is incorporated herein by reference in its entirety. Crystalline Form A is characterized by at least three X-ray powder diffraction peaks at 2Θ angles selected from 4.4°, 9.9°, 2.3° and 22.0°; crystalline Form B is characterized by at least three X-ray powder diffraction peaks at 2Θ angles selected from 9.4°, 11.1°, 16.5°, 18.3° and 18 8°; crystalline Form C is characterized by at least three X-ray diffraction peaks at 2Θ angles selected from 3.7°, 11.2°, 12.1° and 18.6°; and crystalline Form D is characterized by at least three X-ray powder diffraction peaks at 2Θ angles selected from 3.7°, 7.3°, 10.9°, 18.3° and 2.9°.

FIG. 1 shows an XRPD pattern of the crystalline form ZL described herein. An XRPD pattern that is "substantially in accordance" with one or more figures herein showing an XRPD pattern or diffractogram is an XRPD pattern that would be considered by one skilled in the art to represent the same crystalline form of the compound represented by Structural Formula 1 as the sample of the compound represented by Structural Formula 1 that provided the XRPD pattern of one or more figures provided herein. Thus, an XRPD pattern that is substantially in accordance may be identical to that of one of the figures or, more likely, may be somewhat different from one or more of the figures. An XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern of the sample and the corresponding XRPD pattern disclosed herein.

It is to be understood that any 20 angle specified herein means the specified value±0.2°. For example, when a described embodiment or a claim specifies a 20 of 4.4°, this is to be understood to mean 4.4°±0.2°, that is, a 2θ angle of from 4.2° to 4.6°.

The crystalline form ZL provided herein can also be identified on the basis of differential scanning calorimetry (DSC) and/or thermogravimetric analysis (TGA). DSC is a thermoanalytical technique in which the difference in the amount of heat required to increase the temperature of a sample is measured as a function of temperature. DSC can be used to detect physical transformations, such as phase transitions, of a sample. For example, DSC can be used to detect the temperature(s) at which a sample undergoes crystallization, melting or glass transition.

TGA is a method of thermal gravimetric analysis in which changes in physical and chemical properties of a material are measured as a function of increasing temperature (with constant heating rate) or as a function of time (with constant temperature and/or constant mass loss). TGA can provide information about physical phenomena, such as second-order phase transitions, or about chemical phenomena, such as desolvation and/or decomposition.

Figure 2:
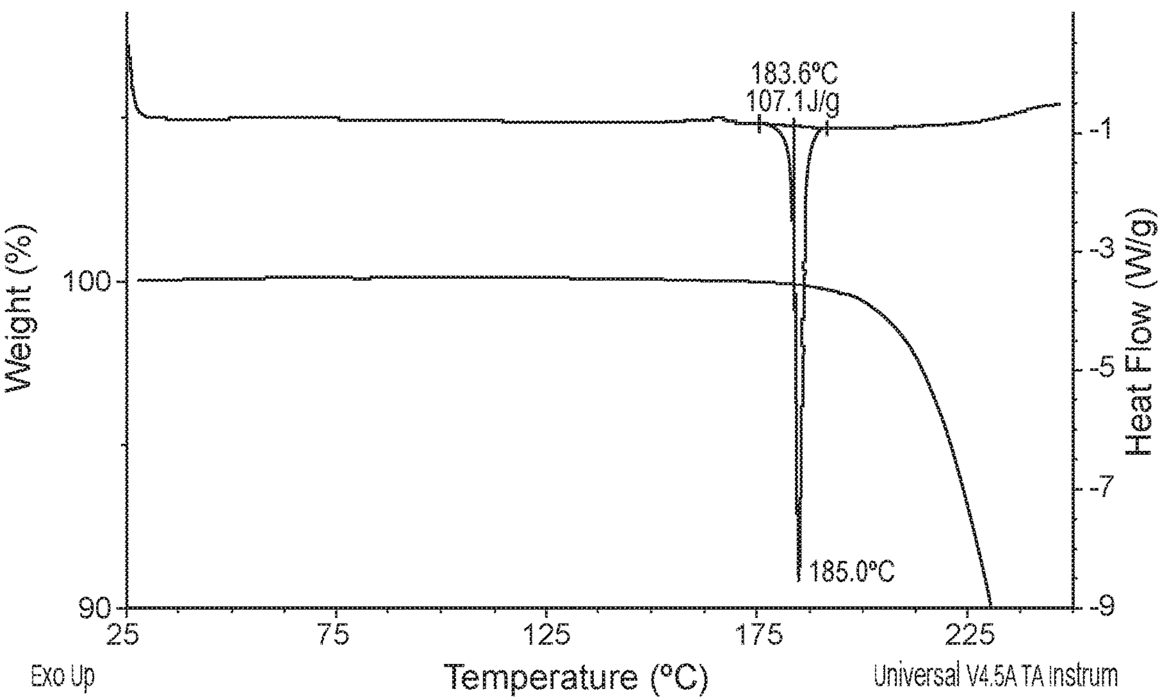
FIG. 2 is a graph depicting a differential scanning calorimetry (DSC) thermogram and a thermogravimetric analysis (TGA) thermogram of the crystalline Form ZL of the compound represented by Structural Formula 1.
Figure 3:
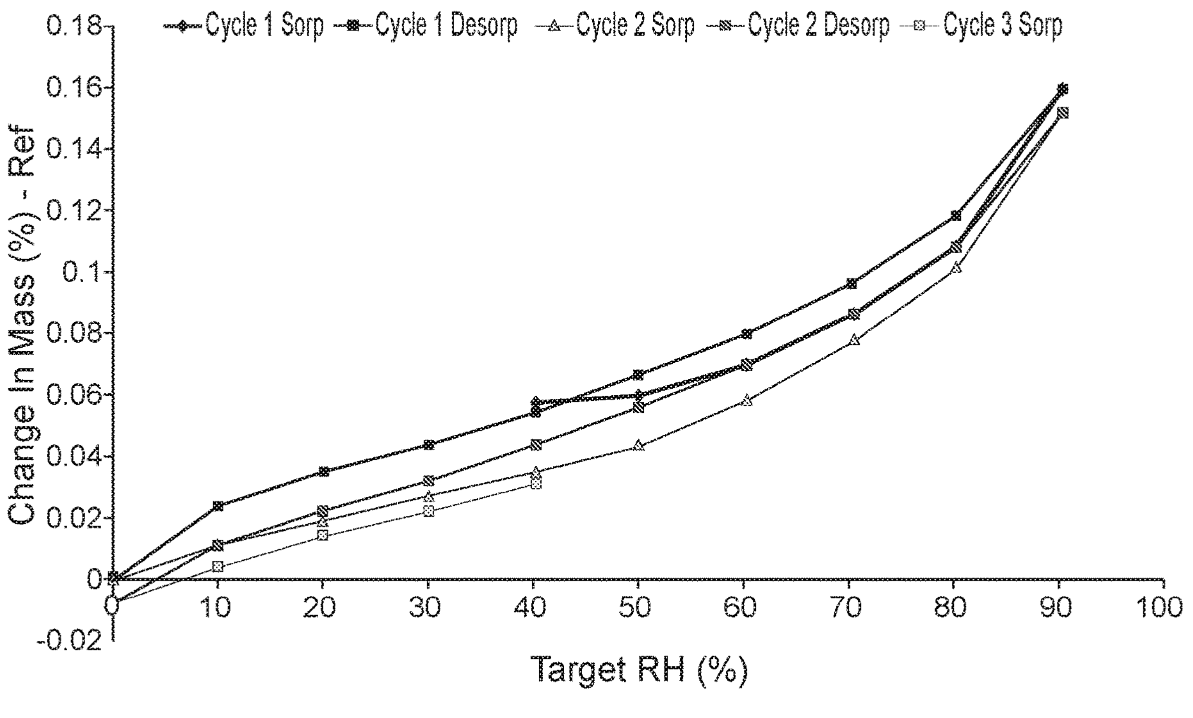
FIG. 3 is a dynamic vapor sorption (DVS) pattern of the crystalline Form ZL of the compound represented by Structural Formula 1.

FIG. 2 shows a DSC thermogram of the crystalline form ZL described herein. FIG. 3 shows a TGA thermogram of the crystalline form ZL described herein. A DSC or TGA thermogram that is "substantially in accordance" with one or more figures herein showing a DSC or TGA thermogram is a DSC or TGA thermogram that would be considered by one skilled in the art to represent the same crystalline form of the compound represented by Structural Formula 1 as the sample of the compound represented by Structural Formula 1 that provided the DSC or TGA thermogram of one or more figures provided herein.

It is to be understood that any temperature associated with DSC or TGA specified herein means the specified value±5° C. or less. For example, when an embodiment or a claim specifies an endothermic peak at about 184° C., this is to be understood to mean 184° C.±5° C. or less, that is a temperature of from 179° C. to 189° C. In preferred embodiments, a DSC or TGA temperature is the specified value±3° C., in more preferred embodiments, ±2° C.

The crystalline form provided can be additionally characterized by dynamic vapor sorption (DVS), wherein a sample is subjected to varying conditions of humidity and temperature, and the response of the sample is measured gravimetrically. The result of a DVS analysis particularly can be a dual curve providing sample weight percent as a function of relative humidity (RH) over time, a dual curve providing sample water content as a function of RH over time, a curve providing weight percent in relation to RH, or a curve providing water content in relation to RH. Equipment useful for measuring such data is known in the art, and any such equipment can be used to measure the compounds according to the present disclosure. In certain embodiments, DVS analysis can be carried out by scanning at a series of specific RH values. Thus, specific polymorphs according to the disclosure may be identified and described in relation to the representative graph and/or the approximate peaks obtained in DVS analysis, particularly scanning from 0% to 95% RH with a step interval of 5% or 10% RH.

Figure 4:
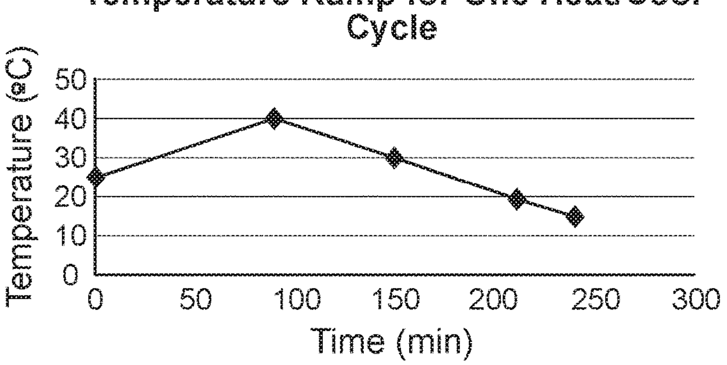
FIG. 4 is a graph of the temperature ramp cycle employed in Method A of the preparation of the crystalline Form ZL of the compound represented by Structural Formula 1.

FIG. 4 shows a DVS pattern of the crystalline form ZL described herein. A DVS pattern that is "substantially in accordance" with one or more figures herein showing a DVS patterns is a DVS pattern that would be considered by one skilled in the art to represent the same crystalline form of the compound represented by Structural Formula 1 as the sample of the compound represented by Structural Formula 1 that provided the DVS pattern of one or more figures provided herein.

Form ZL:

In a first embodiment, a crystalline form of a compound represented by the compound represented by Structural Formula 1 is provided, wherein the crystalline form is Form ZL, and is characterized by x-ray powder diffraction peaks at 2θ angles of 18.75°, 20.16°, 21.37°, and 23.49°, or by x-ray powder diffraction peaks at 2θ angles of 18.75°, 20.16°, 21.37°, 23.49°, and 24.16°, or by x-ray powder diffraction peaks at 2θ angles of 14.00°, 18.75°, 20.16°, 21.37°, 22.55°, 23.49°, 24.16°, and 27.21°, or by x-ray powder diffraction peaks at 2θ angles of 14.00°, 15.89°, 16.77°, 18.75°, 20.16°, 20.72°, 20.98°, 21.37°, 22.55°, 22.96°, 23.49°, 24.16°, 27.21°, and 28.99°. In some embodiments, crystalline Form ZL is characterized by an x-ray powder diffraction pattern substantially in accordance with that depicted in FIG. 1.

Figure 8:
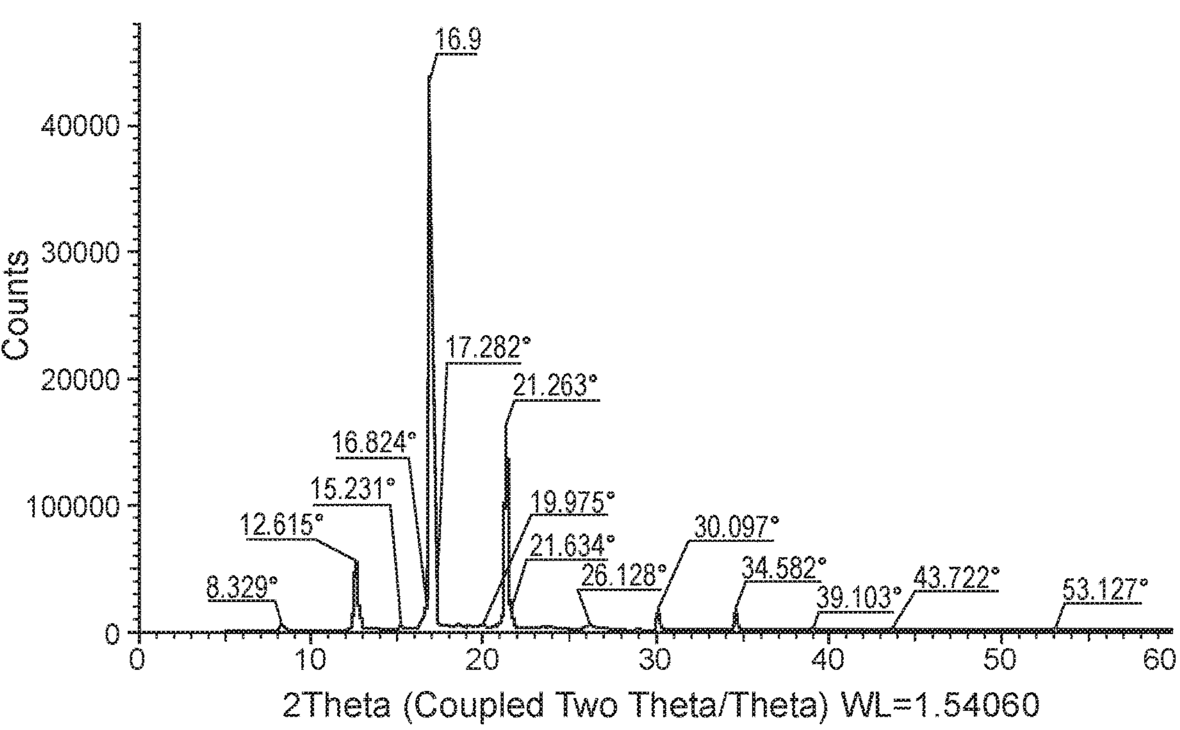
FIG. 8 is an XRPD diffractogram of the aggregates of plate-like crystals of crystalline Form ZL of the compound represented by Structural Formula 1 obtained in reflectance mode (Sample was not ground prior to analysis and reflectance mode was used).
Figure 9:
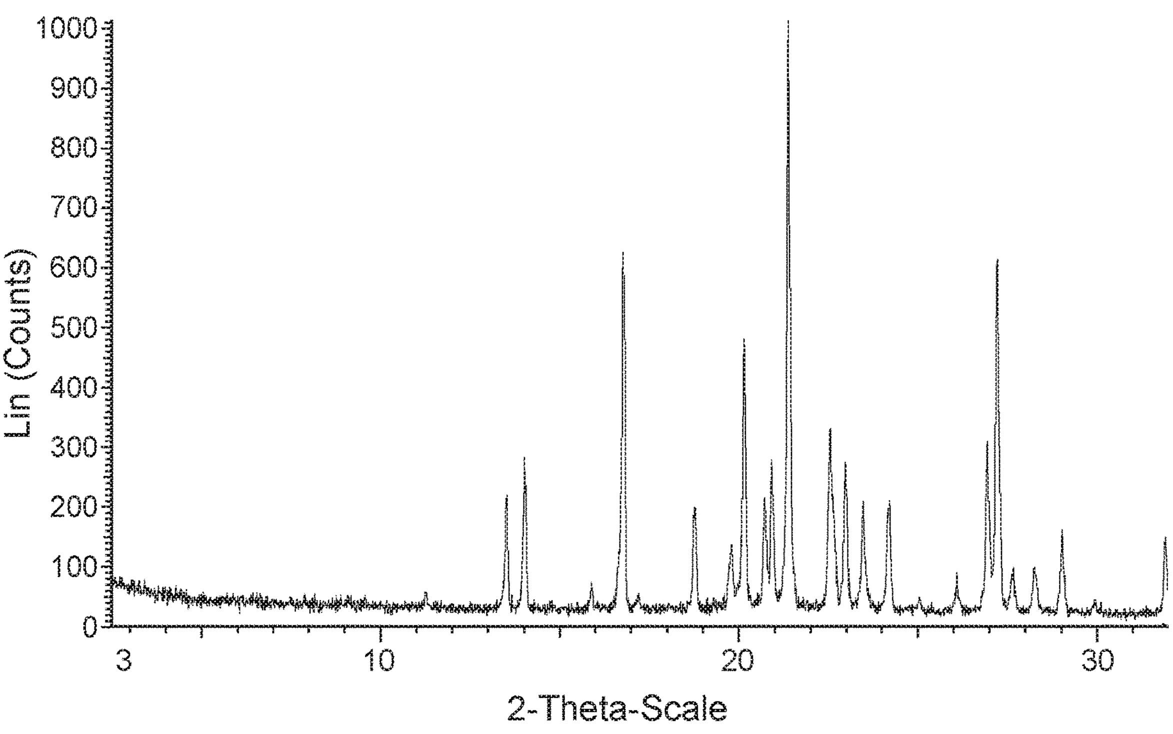
FIG. 9 is an XRPD diffractogram of the aggregates of plate-like crystals of crystalline Form ZL of the compound represented by Structural Formula 1 obtained in transmittance mode (Sample was not ground prior to analysis and transmittance mode was used).

The XRPD pattern depicted in FIG. 1 was obtained from crystalline Form ZL, wherein the XRPD test material was ground prior to conducting the XRPD analysis. It has been observed that when crystalline Form XL is not ground prior to XRPD analysis, XRPD patterns (see FIG. 8 and FIG. 9) distinct from that of FIG. 1 may be obtained. The alternate XRPD pattern depicted in FIG. 8, which exhibits substantially fewer prominent peaks than the pattern of FIG. 1 does, was obtained from analysis of unground plate-like crystals of Form ZL in reflectance mode. The alternate XRPD pattern depicted in FIG. 9, which also lacks some peaks that are evident in the pattern of FIG. 1, was obtained from analysis of unground plate-like crystals of Form ZL in transmittance mode. The variation evident among the patterns of FIG. 1, FIG. 8, and FIG. 9 is a result of an analytical artifact wherein particular reflection planes within the crystal lattice of Form ZL are over- or underrepresented in observed patterns due to the orientation of crystals in the test samples. Unground crystals of Form ZL may settle on a flat surface (e.g., a sample holder used for XRPD analysis) in preferred orientations by virtue of the plate-like crystal habit of certain samples of crystalline Form ZL.

The XRPD patterns of FIG. 1, FIG. 8., and FIG. 9 all correspond to crystalline Form ZL as described and prepared herein. The patterns of FIG. 8 and FIG. 9 represent the extremes of over- and underrepresentation of the particular reflections described above, respectively. True XRPD patterns of Form ZL will be recognized by a person skilled in the art as those that contain any admixture of peaks ranging from the list of FIG. 8 to the list of FIG. 9. By grinding Form ZL test samples prior to analysis, the propensity of plate-like crystals contained therein to stack on one another face-to-face is reduced, thus attenuating preferred orientation effects and leading to diffractograms intermediate between FIG. 8 and FIG. 9, as exemplified by FIG. 1.

Crystalline form ZL in its native state (unground) and exhibiting plate-like crystal habit is characterized by x-ray powder diffraction peaks at 2θ angles 12.61°, 16.90°, 21.26°, and 34.58°, or by x-ray powder diffraction peaks at 2θ angles 8.33°, 12.61°, 15.23°, 16.62°, 16.90°, 17.28°, 19.97°, 21.26°, 21.63°, 30.10°, 34.58°, 39.10°, 43.57°, and 53.13°, especially when analyzed in reflectance mode.

In some embodiments, crystalline form ZL in its native state (unground) and exhibiting plate-like crystal habit is characterized by an x-ray powder diffraction pattern substantially in accordance with that depicted in FIG. 8, especially when analyzed in reflectance mode.

Crystalline Form ZL may be further characterized by a differential scanning calorimetry thermogram comprising a sharp endothermic peak at 184° C., consistent with melting. In some embodiments, the TGA thermogram and/or the DSC thermogram are substantially in accordance with those in FIG. 2 or FIG. 5.

Crystalline Form ZL can be additionally characterized by dynamic vapor sorption pattern comprising a weight gain of about 0.16% at 90% RH. In some embodiments the DVS pattern is substantially in accordance with the one found in FIG. 3.

Pharmaceutical Compositions

In another embodiment, the disclosure relates to a pharmaceutical composition, comprising crystalline Form ZL of the compound represented by the Structural Formula 1:

(1)

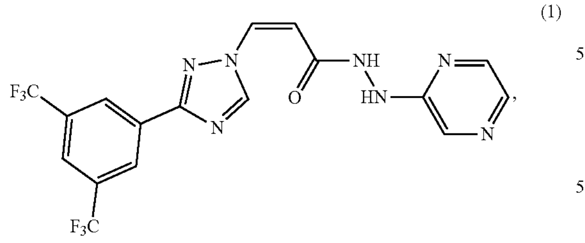

and a pharmaceutically acceptable carrier or diluent. In certain embodiments, the crystalline Form ZL is characterized by x-ray powder diffraction peaks at 2θ angles 18.75°, 20.16°, 21.37°, and 23.49°.

In certain embodiments, the pharmaceutical compositions include crystalline form ZL characterized by x-ray powder diffraction peaks at 2θ angles of 18.75°, 20.16°, 21.37°, and 23.49°, or by x-ray powder diffraction peaks at 2θ angles of 18.75°, 20.16°, 21.37°, 23.49°, and 24.16°, or by x-ray powder diffraction peaks at 2θ angles of 14.00°, 18.75°, 20.16°, 21.37°, 22.55°, 23.49°, 24.16°, and 27.21°, or by x-ray powder diffraction peaks at 2θ angles of 14.00°, 15.89°, 16.77°, 18.75°, 20.16°, 20.72°, 20.98°, 21.37°, 22.55°, 22.96°, 23.49°, 24.16°, 27.21°, and 28.99°.

In certain embodiments, the pharmaceutical compositions include the crystalline form ZL characterized by an x-ray powder diffraction pattern substantially in accordance with that depicted in FIG. 1.

The term "pharmaceutically acceptable carrier" means a non-toxic solvent, dispersant, excipient, adjuvant or other material which is mixed with the active ingredient in order to permit formation of a pharmaceutical composition, i.e., a dosage form capable of being administered to a subject. A "pharmaceutically acceptable carrier" should not destroy the activity of the compound with which it is formulated. Pharmaceutically acceptable carriers are well known in the art.

Pharmaceutically acceptable carriers, adjuvants or vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutical compositions of the disclosure may be administered orally, parenterally (including subcutaneous, intramuscular, intravenous and intradermal), by inhalation spray, topically, rectally, nasally, buccally, vaginally or via an implanted reservoir. In some embodiments, provided pharmaceutical compositions are administrable intravenously and/or intraperitoneally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the pharmaceutical compositions are administered orally, subcutaneously, intraperitoneally or intravenously. Sterile injectable forms of the pharmaceutical compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutical compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Specific pharmaceutically acceptable carriers suitable for use in an oral formulation such as a tablet or capsule include, but are not limited to, microcrystalline cellulose (Avicel PH101), croscarmellose Sodium (Ac-Di-Sol), kollidon 30 powder (polyvinylpyrrolidone, povidone), colloidal silicon dioxide M5-P, magnesium stearate, microcrystalline cellulose (Avcel PH102), sodium lauryl sulfate (Kolliphor SLS Fine) and Colloidal Silicon Dioxide M5-P. Each of the above listed carriers can be used in an oral formulation either alone or in any combination.

Further pharmaceutically acceptable carriers suitable for use in an oral formulation such as a tablet or capsule include, but are not limited to, microcrystalline cellulose (Avicel PH112), crospovidone (polyplasdone XL-10), colloidal silicone dioxide (Cab-O-Sil M-5P), Talc, starch and calcium stearate. In a particular aspect, the crystalline form ZL is present in the oral formulation from about 25-45% by weight (freebase weight). In other aspects, Disodium EDTA is also present in the oral formulation. In certain aspects, the EDTA increases the bioavailability of the active. In a particular embodiment, the bioavailability of the active is increased by from about 1.5 fold to about 20 fold (e.g., 1.5, 2, 3, 4, 5, 6, 7, 8, 9, 10, 11, 12, 13, 14, 15, 16, 17, 18, 19 or 20 fold). When EDTA is present in the formulation, the w/w ratio of the crystalline form (freebase weight) to EDTA ranges from about 1:0.25 to about 1:15 (e.g., 1:0.25, 1:0.5, 1:1, 1:2.5, 1:5, 1:10, or 1:15). For ophthalmic use, provided pharmaceutical compositions may be formulated as micronized suspensions or in an ointment such as petrolatum.

Pharmaceutical compositions of this disclosure may also be administered by nasal aerosol or inhalation.

In some embodiments, pharmaceutical compositions of this disclosure are formulated for intra-peritoneal administration.

The amount of the crystalline form of a compound represented by the compound represented by Structural Formula 1 in pharmaceutical compositions of this disclosure is such that is effective to measurably treat or prevent in the treatment of disorders associated with CRM1 activity in a subject. In certain embodiments, a pharmaceutical composition of this disclosure is formulated for administration to a subject in need of such pharmaceutical composition. The term "subject," as used herein, can be a human subject or an animal.

The amount of the crystalline form ZL may be combined with the pharmaceutically acceptable carrier materials to produce a pharmaceutical composition in a single dosage form will vary depending upon the host treated and/or the particular mode of administration. In one embodiment, the pharmaceutical compositions should be formulated so that a dosage of between 0.01-100 mg/kg body weight/day of the compound of Structural Formula 1 can be administered to a patient receiving these compositions. In another embodiment, the dosage is from about 0.5 to about 100 mg/kg of body weight, or between 1 mg and 1000 mg/dose, every 4 to 120 hours, or according to the requirements of the particular drug. Typically, the pharmaceutical compositions of this disclosure will be administered from about 1 to about 6 times per day. Exemplary doses, include but are not limited to, 1.0 mg/kg twice a day for about 4-14 days and 1.5 mg/kg once a day for 5 to 10 days.

In certain embodiments, the pharmaceutical composition of crystalline form ZL can be formulated to deliver to the subject the dosage of the compound represented by Structural Formula (I) of 80 mg (45 mg/$m^2$ BSA), delivered, for example, twice weekly. In alternative embodiments, the pharmaceutical composition of crystalline form ZL can be formulated to deliver to the subject the dosage of the compound represented by Structural Formula (I) of 100 mg, delivered, for example, once per day on selected days of a treatment cycle.

It should also be understood that a specific dosage and treatment regimen for any particular subject (e.g., patient) will depend upon a variety of factors, including the age, body weight, general health, sex, diet, time of administration, rate of excretion, drug combination, and the judgment of the treating physician and the severity of the particular disease being treated.

Upon improvement of a subject's condition, a maintenance dose of a pharmaceutical composition of this disclosure may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Treatment and Uses for Crystalline Form ZL and Pharmaceutical Compositions Comprising Same Crystalline form ZL of the compound represented by Structural Formula (I) and pharmaceutical compositions comprising same are generally useful for the inhibition of CRM1 and are, therefore, useful for treating one or more disorders associated with activity of CRM1. Thus, in certain embodiments, the present disclosure provides a method for treating a disorder associated with CRM1 activity, comprising administering to a subject in need thereof a therapeutically effective amount of crystalline form ZL or a pharmaceutical composition described herein. Crystalline form ZL and pharmaceutical composition comprising same can also be administered to cells in culture, e.g., in vitro or ex vivo, or to a subject, e.g., in vivo, to treat, prevent, and/or diagnose a variety of disorders, including those described hereinbelow.

The activity of crystalline form ZL and a pharmaceutical composition comprising same as an inhibitor of CRM1 may be assayed in vitro, in vivo or in a cell line. Detailed conditions for assaying an inhibitor of CRM1, such as crystalline form ZL of the compound represented by Structural Formula (I), are set forth in U.S. Pat. No. 9,079,865.

The term "treat" or "treating" means to alleviate symptoms, eliminate the causation of the symptoms, either on a temporary or permanent basis, or to prevent or slow the appearance of symptoms of the named disorder or condition.

The term "CRM1-mediated" disorder or condition or "disorder associated with CRM1 activity," as used herein, means any disease or other deleterious condition in which CRM1 is known to play a role. Accordingly, another embodiment of the present disclosure relates to treating or lessening the severity of one or more diseases in which CRM1 is known to play a role. In some embodiments, the present disclosure provides methods of treating a disease associated with expression or activity of p53, p73, p21, pRB, p27, INB, NFNB, c-Abl, FOXO proteins, COX-2, or an HDAC (histone deacetylases) in a subject comprising administering to the subject a therapeutically effective amount of a pharmaceutical composition described herein. In another embodiment, the present disclosure relates to a method of treating or lessening the severity of a disease or condition selected from a proliferative disorder (e.g., cancer), an inflammatory disorder, an autoimmune disorder, a viral infection, an ophthalmological disorder or a neurodegenerative disorder wherein said method comprises administering to a patient in need thereof a compound or composition according to the present disclosure. In a more specific embodiment, the present disclosure relates to a method of treating or lessening the severity of cancer. Specific examples of the above disorders are set forth in detail below.

The term "therapeutically effective amount" means an amount of crystal form ZL of the compound represented by Structural Formula (I) that is effective in treating or lessening the severity of one or more symptoms of a disorder or condition. In the case of promoting wound healing, a therapeutically effective amount is an amount that promotes healing of a wound.

As used herein, the term "prophylaxis" or "prophylactic" refer to measures taken to preventing or increasing resistance to a disease prior to its onset as well as to measures that ameliorate the symptoms of a disease when taken prior to its onset. Prophylaxis also includes measures taken to prevent the recurrence of a disease.

The term "prophylactically effective amount" means an amount of crystal form ZL of the compound represented by Structural Formula (I) that is effective for prophylaxis of a condition treatable by such compound.

As used herein, "promoting wound healing" means treating a subject with a wound and achieving healing, either partially or fully, of the wound. Promoting wound healing can mean, e.g., one or more of the following: promoting epidermal closure; promoting migration of the dermis; promoting dermal closure in the dermis; reducing wound healing complications, e.g., hyperplasia of the epidermis and adhesions; reducing wound dehiscence; and promoting proper scab formation.

In some embodiments, the present disclosure relates to a method for promoting wound healing in a subject in need thereof, comprising administering to the subject in need thereof a therapeutically effective amount of crystal form ZL of the compound represented by Structural Formula (I) or a pharmaceutical composition described herein.

Cancers treatable by crystalline form ZL or pharmaceutical compositions described herein include, but are not limited to, hematologic malignancies (leukemias, lymphomas, myelomas including multiple myeloma, myelodysplastic and myeloproliferative syndromes) and solid tumors (carcinomas such as prostate, breast, lung, colon, pancreatic, renal, ovarian as well as soft tissue and osteosarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple. In one embodiment, the cancer is multiple myeloma.

Inflammatory disorders treatable by crystalline form ZL or pharmaceutical compositions described herein include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by crystalline form ZL or pharmaceutical compositions described herein include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this disclosure also include chronic viral infections, including hepatitis B and hepatitis C. Additionally, viral diseases treatable by the compounds of this disclosure include infections caused by a coronavirus, e.g., SARS, MERS, and SARS-CoV-2.

Exemplary ophthalmology disorders include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by crystalline form ZL or pharmaceutical compositions described herein include, but are not limited to, Parkinson's, Alzheimer's, and Huntington's, and Amyotrophic lateral sclerosis (ALS/Lou Gehrig's Disease).

Crystalline form ZL or pharmaceutical compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Crystalline form ZL or pharmaceutical compositions described herein may also be used to treat disorders related to food intake such as obesity and hyperphagia.

In another embodiment, crystalline form ZL or pharmaceutical compositions described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

In some embodiments, the disorder or condition associated with CRM1 activity is beta-thalassemia, muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospirosis renal disease, glaucoma, retinal disease, ageing, headache, pain, complex regional pain syndrome, cardiac hypertrophy, muscle wasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, Behcet's disease, incontinentia pigmenti, tuberculosis, asthma, Crohn's disease, colitis, ocular allergy, appendicitis, Paget's disease, pancreatitis, periodonitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, Parkinson's disease, multiple sclerosis, Alzheimer's disease, amyotropic lateral sclerosis, Huntington's disease, cataracts, or hearing loss.

In other embodiments, the disorder or condition associated with CRM1 activity is head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

In further aspects, the present disclosure relates to a use of crystalline form ZL or pharmaceutical compositions described herein for the manufacture of a medicament for the treatment of a disorder associated with CRM1 activity. The present disclosure also relates to crystalline form ZL or pharmaceutical compositions described herein for use in treating a disorder associated with CRM1 activity. Specific examples of disorders associated with CRM1 activity are as set forth in detail herein.

In yet further aspects, the present disclosure relates to a use of crystalline form ZL or pharmaceutical compositions described herein for the manufacture of a medicament for the treatment of a disease associated with expression or activity of p53, p73, p21, pRB, p27, INB, NFNB, c-Abl, FOXO proteins, COX-2 or an HDAC in a subject. In some embodiments, the present disclosure relates to a use of crystalline form ZL or pharmaceutical compositions described herein in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthalmologic disorders.

In some embodiments, the present disclosure relates to a method for inhibiting CRM1 in a biological sample comprising contacting the biological sample with, or administering to the patient, crystalline form ZL or pharmaceutical compositions described herein.

Neoplastic Disorders

Crystalline form ZL or pharmaceutical compositions described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

Crystalline form ZL or pharmaceutical compositions described herein are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. Crystalline form ZL or pharmaceutical compositions described herein are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macroglobulinemia; and Wilms' Tumor.

Further exemplary cancers include diffuse large B-cell lymphoma (DLBCL) and mantle cell lymphoma (MCL). Yet further exemplary cancers include endocervical cancer, B-cell ALL, T-cell ALL, B- or T-cell lymphoma, mast cell cancer, glioblastoma, neuroblastoma, follicular lymphoma and Richter's syndrome.

Exemplary sarcomas include fibrosarcoma, alveolar soft part sarcoma (ASPS), liposarcoma, leiomyosarcoma, chondrosarcoma, synovial sarcoma, chordoma, spindle cell sarcoma, histiocytoma, rhabdomyosarcoma, Ewing's sarcoma, neuroectodermal sarcoma, phyllodes/osteogenic sarcoma and chondroblastic osteosarcoma.

Metastases of the aforementioned cancers can also be treated or prevented in accordance with the methods described herein.

In some embodiments, the disclosure relates to a method for treating or preventing a CRM1-associated disease or disorder, the method comprising administering to a subject in need thereof a therapeutically or prophylactically effective amount of crystal form ZL of the compound represented by Structural Formula (I) or a pharmaceutical composition described herein.

In certain embodiments, the disorder is a proliferative disorder, cancer, an inflammatory disorder, an autoimmune disorder, a viral infection, an ophthalmological disorder, a neurodegenerative disorder, a disorder of abnormal tissue growth, a disorder related to food intake, an allergic disorder, or a respiratory disorder. For example, the disorder is cancer.

In some embodiments, the cancer is multiple myeloma, relapsed or refractory multiple myeloma, penta-refractory multiple myeloma, acute myeloid leukemia, relapsed or refractory acute myeloid leukemia, secondary acute myeloid leukemia, diffuse large B-cell lymphoma, relapsed or refractory diffuse large B-cell lymphoma, recurrent or refractory B-cell non-Hodgkin lymphoma, recurrent or refractory extranodal marginal zone lymphoma, recurrent follicular lymphoma, recurrent or refractory indolent adult non-Hodgkin lymphoma, recurrent or refractory mantle cell lymphoma, recurrent or refractory marginal zone lymphoma, recurrent or refractory small lymphocytic lymphoma, recurrent Waldenstrom macroglobulinemia, non-Hodgkin lymphoma, transformed recurrent non-Hodgkin lymphoma, peripheral T-cell lymphoma, cutaneous T-cell lymphoma, neuroendocrine carcinoma, non-small cell lung cancer, liposarcoma, dedifferentiated liposarcoma, malignant peripheral nerve sheath tumors, alveolar soft part sarcoma, Ewing sarcoma, soft tissue sarcoma, breast cancer, ovarian cancer, ovarian carcinoma, endometrial cancer, endometrial carcinoma, cervical carcinoma, glioblastoma, glioma, malignant glioma, recurrent brain neoplasm, recurrent childhood central nervous system neoplasm, recurrent childhood glioblastoma, refractory central nervous system neoplasm, multiple myeloma, refractory multiple myeloma, thymoma, advanced thymic epithelial tumor, de novo myelodysplastic syndrome, myelodysplastic syndrome, secondary myelodysplastic syndrome, esophageal cancer, gastric cancer, hormone-resistant prostate cancer, metastatic prostate carcinoma in the soft tissue, prostate adenocarcinoma, recurrent melanoma, leukemia, relapsed acute lymphoblastic leukemia (ALL), refractory ALL, relapsed acute myelogenous leukemia (AML), refractory AML, prolymphocytic leukemia, relapsed mixed lineage leukemia, refractory mixed lineage leukemia, relapsed biphenotypic leukemia, refractory biphenotypic leukemia, chronic myelogenous leukemia (CML) in blast crisis, refractory chronic lymphocytic leukemia, mixed phenotype acute leukemia, squamous cell carcinoma, recurrent small cell lung carcinoma, recurrent squamous cell lung carcinoma, colorectal neoplasm, acinar cell adenocarcinoma of the pancreas, duct cell adenocarcinoma of the pancreas, pancreatic cancer, or salivary gland cancer. For example, the cancer is refractory multiple myeloma, such as penta-refractory multiple myeloma.

Combination Therapies

In some embodiments, crystalline form ZL or pharmaceutical compositions described herein are administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents to a subject in need thereof to treat any one or more indications described herein. For example, crystalline form ZL or pharmaceutical compositions described herein may be administered with another therapeutic agent simultaneously or sequentially in separate unit dosage forms or together in a single unit dosage form. Accordingly, the present disclosure relates to a single unit dosage form comprising crystalline form ZL or pharmaceutical compositions described herein, an additional therapeutic agent, and a pharmaceutically acceptable carrier.

In one embodiment of the disclosure, where a second therapeutic agent is administered to a subject, the effective amount of crystalline form ZL of the compound represented by Structural Formula 1 is less than its effective amount would have been if the second therapeutic agent were not administered. In another embodiment, the effective amount of the second therapeutic agent is less than its effective amount would have been if crystalline form ZL of the compound represented by Structural Formula 1 were not administered. In this way, undesired side effects associated with high doses of either agent may be minimized. Other potential advantages (including without limitation improved dosing regimens and/or reduced drug cost) will be apparent to those of skill in the art. The additional agents may be administered separately from crystalline form ZL or pharmaceutical compositions described herein, as part of a multiple dose regimen. Alternatively, those agents may be part of a single dosage form, mixed together with crystalline form ZL or pharmaceutical compositions described herein.

In certain embodiments, crystalline form ZL or pharmaceutical compositions described herein may be administered alone or in combination with other compounds useful for treating or preventing inflammation. Exemplary anti-inflammatory agents include, for example, steroids (e.g., Cortisol, cortisone, fludrocortisone, prednisone, 6 [alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa. In a specific embodiment, crystalline form ZL or pharmaceutical compositions described herein are administered in combination with dexamethasone.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiments, crystalline form ZL or pharmaceutical compositions described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, crystalline form ZL or pharmaceutical compositions described herein are administered in combination with an anthracycline or a Topo II inhibitor. In certain embodiments, crystalline form ZL or pharmaceutical compositions described herein are administered in combination with Doxorubicin (Dox). In certain embodiments, crystalline form ZL or pharmaceutical compositions described herein are administered in combination with bortezomib (and more broadly including carfilzomib).

Cancer Combination Therapies

In some embodiments, the compound represented by Structural Formula 1 or (single) crystalline form thereof, (e.g., in a pharmaceutical composition described herein) is administered together with an additional cancer treatment. Exemplary additional cancer treatments include, for example: chemotherapy, targeted therapies such as antibody therapies, kinase inhibitors, immunotherapy, and hormonal therapy, epigenetic therapy, proteosome inhibitors, and anti-angiogenic therapies. Examples of each of these treatments are provided below. As used herein, the term "combination," "combined," and related terms refer to the simultaneous or sequential administration of therapeutic agents in accordance with this disclosure. For example, the compound represented by Structural Formula 1 can be administered with another therapeutic agent simultaneously or sequentially in separate unit dosage forms or together in a single unit dosage form. Accordingly, the present disclosure provides a single unit dosage form comprising the compound represented by Structural Formula 1 (e.g., a crystalline form or single crystalline form of the compound of Structural Formula 1), an additional therapeutic agent, and a pharmaceutically acceptable carrier.

The amount of both the compound represented by Structural Formula 1 and additional therapeutic agent (in those pharmaceutical compositions which comprise an additional therapeutic agent as described above) that can be combined with the carrier materials to produce a single dosage form will vary depending upon the host treated and the particular mode of administration. Preferably, pharmaceutical compositions of this disclosure should be formulated so that a dosage of between 0.01-100 mg/kg body weight/day of a compound of Structural Formula 1 can be administered.

Chemotherapy

In some embodiments, crystalline form ZL or pharmaceutical compositions described herein are co-administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carfilzomib, Carmofur, Carmustine, Celecoxib, Cetuximab, Chlorambucil, Chlormethine, CHOEP-21, CHOP, Cisplatin, Cladribine, Clofarabine, Crisantaspase, Cyclophosphamide, Cytarabine or ara-C, Dacarbazine, Dactinomycin, DA EPOCH, Daratumumab, Daunorubicin, Decitabine, Demecolcine, Dexamethasone, Docetaxel, Doxorubicin, Efaproxiral, Elesclomol, Elsamitrucin, Enocitabine, Epirubicin, Eribulin, Estramustine, Etoglucid, Etoposide, FLAG (Flu+Cyt), Floxuridine, Fludarabine, Fluorouracil (5FU), FOLFOX, Fotemustine, Gemcitabine, gemcitabine-oxaliplatin (GemOx), Gliadel implants, Hydroxycarbamide, Hydroxyurea, Ibrutinib, Idarubicin, Ifosfamide, Irinotecan, Irofulven, Ixabepilone, Ixazomib, Larotaxel, Lenalidomide, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nab-paclitaxel, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, PLD (pegylated liposomal doxorubicin), Plicamycin, Pomalidomide, Porfimer sodium, Prednimustine, Procarbazine, Raltitrexed, Ranimustine, R-CHOP, r-dhaox, r-dhap, Rituximab, Romidepsin Rubitecan, Sapacitabine, Semustine, Sitimagene ceradenovec, Sorafonib, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Targeted Therapy

Crystalline form ZL or pharmaceutical compositions described herein can be used in combination with or as a part of a targeted therapy. Targeted therapy constitutes the use of agents specific for the target of interest (e.g., a deregulated protein) in cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a pharmaceutical composition described herein, e.g., Gleevec® (imatinib) (Vignari and Wang 2001).

Targeted therapy can also involve small peptides as "homing devices" which can bind to cell surface receptors or affected extracellular matrix surrounding the tumor.

Radionuclides which are attached to these peptides (e.g., RGDs) eventually kill the cancer cell if the nuclide decays in the vicinity of the cell. An example of such therapy includes BEXXAR® (tositumomab).

Angiogenesis

Crystalline form ZL or pharmaceutical compositions described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularization or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Crystalline form ZL or pharmaceutical compositions described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, D-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including 06-methylguanine-DNA methyltransferase (MGMT), MLH1 cyclin-dependent kinase inhibitor 2B (CDKN2B), and RASSFIA. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucleotides and siRNA.

Immunotherapy

In some embodiments, crystalline form ZL or pharmaceutical compositions described herein are administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge® (sipuleucel-T), and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agent(s) can be used in combination with crystalline form ZL or pharmaceutical compositions described herein.

Hormonal Therapy

In some embodiments, crystalline form ZL or pharmaceutical compositions described herein are administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a pharmaceutical composition described herein.

Hormonal therapy agents include the administration of hormone agonists or hormone antagonists and include retinoids/retinoic acid, compounds that inhibit estrogen or testosterone, as well as administration of progestogens.

Inflammation and Autoimmune Disease

Crystalline form ZL or pharmaceutical compositions described herein may be used to treat or prevent a disease or disorder associated with inflammation, particularly in humans and other mammals. Crystalline form ZL or pharmaceutical compositions described herein may be administered prior to the onset of, at, or after the initiation of inflammation. When used prophylactically, the pharmaceutical compositions are preferably provided in advance of any inflammatory response or symptom. Administration can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, crystalline form ZL or pharmaceutical compositions described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). Crystalline form ZL or pharmaceutical compositions described herein may be used to treat chronic hepatitis infection, including hepatitis B and hepatitis C.

Additionally, crystalline form ZL or pharmaceutical compositions described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, crystalline form ZL or pharmaceutical compositions described herein can be used to treat multiple sclerosis.

Viral Infections

Crystalline form ZL or pharmaceutical compositions described herein may be used to treat or prevent a disease or disorder associated with a viral infection, particularly in humans and other mammals. Crystalline form ZL or pharmaceutical compositions described herein may be administered prior to the onset of, at, or after the initiation of viral infection. When used prophylactically, crystalline form ZL or pharmaceutical compositions described herein can be administered in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, COVID-19, German measles, congenital rubella, Varicella, and herpes zoster.

Exemplary viral influenza A strains include H1N1, H3N2, H5N1, H7N3, H7N9. A compound described herein can also be used to treat or prevent influenza B.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, SARS, MERS, SARS-COV-2, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

Ophthalmology crystalline form ZL or pharmaceutical compositions described herein may be used to treat or prevent an ophthamology disorder. Exemplary ophthamology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Other ophthalmology disorders treatable using crystalline form ZL or pharmaceutical compositions described herein include proliferative vitreoretinopathy and chronic retinal detachment.

Inflammatory eye diseases are also treatable using crystalline form ZL or pharmaceutical compositions described herein.

Neurodegenerative Disease

Crystalline form ZL or pharmaceutical compositions described herein may be used to treat or prevent a neurodegenerative disease. Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics includes antisense oligonucleotides and stem cells.

Wound Healing

Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Crystalline form ZL or pharmaceutical compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present disclosure relates to a method for promoting wound healing in a subject, comprising administering to the subject a therapeutically effective amount of crystalline form ZL or pharmaceutical compositions described herein. The method need not achieve complete healing or closure of the wound; it is sufficient for the method to promote any degree of wound closure. In this respect, the method can be employed alone or as an adjunct to other methods for healing wounded tissue.

Crystalline form ZL or pharmaceutical compositions described herein can be used to treat wounds during the inflammatory (or early) phase, during the proliferative (or middle) wound healing phase, and/or during the remodeling (or late) wound healing phase.

In some embodiments, the subject in need of wound healing is a human or an animal, for example, a dog, a cat, a horse, a pig, or a rodent, such as a mouse.

In some embodiments, crystalline form ZL or pharmaceutical compositions described herein are administered topically, for example, proximate to the wound site, or systemically.

More specifically, a therapeutically effective amount of crystalline form ZL or pharmaceutical compositions described herein can be administered (optionally in combination with other agents) to the wound site by coating the wound or applying a bandage, packing material, stitches, etc., that are coated or treated with the compound or composition described herein. As such, crystalline form ZL or pharmaceutical compositions described herein can be formulated for topical administration to treat surface wounds. Topical formulations include those for delivery via the mouth (buccal) and to the skin such that a layer of skin (i.e., the epidermis, dermis, and/or subcutaneous layer) is contacted with the pharmaceutical composition described herein. Topical delivery systems may be used to administer topical formulations of the compounds and compositions described herein.

Alternatively, crystalline form ZL or pharmaceutical compositions described herein can be administered at or near the wound site by, for example, injection of a solution, injection of an extended release formulation, or introduction of a biodegradable implant comprising the compound or composition described herein.

Crystalline form ZL or pharmaceutical compositions described herein can be used to treat acute wounds or chronic wounds. A chronic wound results when the normal reparative process is interrupted. Chronic wounds can develop from acute injuries as a result of unrecognized persistent infections or inadequate primary treatment. In most cases however, chronic lesions are the end stage of progressive tissue breakdown owing to venous, arterial, or metabolic vascular disease, pressure sores, radiation damage, or tumors.

In chronic wounds, healing does not occur for a variety of reasons, including improper circulation in diabetic ulcers, significant necrosis, such as in burns, and infections. In these chronic wounds, viability or the recovery phase is often the rate-limiting step. The cells are no longer viable and, thus, initial recovery phase is prolonged by unfavorable wound bed environment.

Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions; and/or long-standing wounds. Other examples of chronic wounds include chronic ulcers, diabetic wounds, wounds caused by diabetic neuropathy, venous insufficiencies, and arterial insufficiencies, and pressure wounds and cold and warm burns. Yet other examples of chronic wounds include chronic ulcers, diabetic wounds, wounds caused by diabetic neuropathy, venous insufficiencies, arterial insufficiencies, and pressure wounds.

Acute wounds include, but are not limited to, post-surgical wounds, lacerations, hemorrhoids and fissures.

In a particular embodiment, crystalline form ZL or pharmaceutical compositions described herein can be used for diabetic wound healing or accelerating healing of leg and foot ulcers secondary to diabetes or ischemia in a subject.

In one embodiment, the wound is a surface wound. In another embodiment, the wound is a surgical wound (e.g., abdominal or gastrointestinal surgical wound). In a further embodiment, the wound is a burn. In yet another embodiment, the wound is the result of radiation exposure.

Crystalline form ZL or pharmaceutical compositions described herein can also be used for diabetic wound healing, gastrointestinal wound healing, or healing of an adhesion due, for example, to an operation.

Crystalline form ZL or pharmaceutical compositions described herein can also be used to heal wounds that are secondary to another disease. For example, in inflammatory skin diseases, such as psoriasis and dermatitis, there are numerous incidents of skin lesions that are secondary to the disease, and are caused by deep cracking of the skin, or scratching of the skin. Crystalline form ZL or pharmaceutical compositions described herein can be used to heal wounds that are secondary to these diseases, for example, inflammatory skin diseases, such as psoriasis and dermatitis.

In a further embodiment, the wound is an internal wound. In a specific aspect, the internal wound is a chronic wound. In another specific aspect, the wound is a vascular wound. In yet another specific aspect, the internal wound is an ulcer. Examples of internal wounds include, but are not limited to, fistulas and internal wounds associated with cosmetic surgery, internal indications, Crohn's disease, ulcerative colitis, internal surgical sutures and skeletal fixation. Other examples of internal wounds include, but are not limited to, fistulas and internal wounds associated with cosmetic surgery, internal indications, internal surgical sutures and skeletal fixation.

Examples of wounds include, but are not limited to, abrasions, avulsions, blowing wounds (i.e., open pneumothorax), burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the pharmaceutical compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

In certain embodiments, the wound is selected from the group consisting of a burn wound, an incised wound, an open wound, a surgical or post-surgical wound, a diabetic lesion, a thermal burn, a chemical burn, a radiation burn, a pressure sore, a bedsore, and a condition related to diabetes or poor circulation. In more preferred embodiments, the wound is selected from the group consisting of an incised wound, an open wound, a surgical or post-surgical wound, a diabetic lesion, a pressure sore, a bedsore, and a condition or wound related to diabetes or poor circulation.

In some embodiments, the wound is selected from the group consisting of a non-radiation burn wound, an incised wound, an open wound, a surgical or post-surgical wound, a diabetic lesion, a thermal burn, a chemical burn, a pressure sore, a bedsore, and a condition related to diabetes or poor circulation. In some embodiments, the wound is selected from the group consisting of an incised wound, an open wound, a surgical or post-surgical wound, a diabetic lesion, a pressure sore, a bedsore, and a condition related to diabetes or poor circulation.

The present disclosure also relates to methods for reducing scar formation during wound healing in a subject. Crystalline form ZL or pharmaceutical compositions described herein can be administered directly to the wound or to cells proximate the wound at an amount effective to reduce scar formation in and/or around the wound. Thus, in some embodiments, a method of reducing scar formation during wound healing in a subject is provided, the method comprising administering to the subject a therapeutically effective amount of crystalline form ZL or pharmaceutical compositions described herein.

The wound can include any injury to any portion of the body of a subject.

In certain embodiments, the present disclosure relates to methods for ameliorating, reducing, or decreasing the formation of scars in a subject that has suffered a burn injury. In other embodiments, the present disclosure relates to methods for treating, reducing the occurrence of, or reducing the probability of developing hypertrophic scars in a subject that has suffered an acute or chronic wound or injury.

Other Disorders

Crystalline form ZL or pharmaceutical compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

Combination Radiation Therapy

Crystalline form ZL or pharmaceutical compositions described herein are useful as radiosensitizers. Therefore, pharmaceutical compositions described herein can be administered in combination with radiation therapy. Radiation therapy is the medical use of high-energy radiation (e.g., X-rays, gamma rays, charged particles) to shrink tumors and kill malignant cells, and is generally used as part of cancer treatment. Radiation therapy kills malignant cells by damaging their DNA.

Radiation therapy can be delivered to a patient in several ways. For example, radiation can be delivered from an external source, such as a machine outside the patient's body, as in external beam radiation therapy. External beam radiation therapy for the treatment of cancer uses a radiation source that is external to the patient, typically either a radioisotope, such as $^{60}Co$, $^{137}Cs$, or a high energy X-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

Internal radiation therapy is localized radiation therapy, meaning the radiation source is placed at the site of the tumor or affected area. Internal radiation therapy can be delivered by placing a radiation source inside or next to the area requiring treatment. Internal radiation therapy is also called brachytherapy. Brachytherapy includes intracavitary treatment and interstitial treatment. In intracavitary treatment, containers that hold radioactive sources are put in or near the tumor. The sources are put into the body cavities. In interstitial treatment, the radioactive sources alone are put into the tumor. These radioactive sources can stay in the patient permanently. Typically, the radioactive sources are removed from the patient after several days. The radioactive sources are in containers.

There are a number of methods for administration of a radiopharmaceutical agent. For example, the radiopharmaceutical agent can be administered by targeted delivery or by systemic delivery of targeted radioactive conjugates, such as a radiolabeled antibody, a radiolabeled peptide and a liposome delivery system. In one particular embodiment of targeted delivery, the radiolabelled pharmaceutical agent can be a radiolabelled antibody. See, for example, Ballangrud A. M., et al. Cancer Res., 2001; 61:2008-2014 and Goldenber, D. M. J. Nucl. Med., 2002; 43 (5): 693-713, the contents of which are incorporated by reference herein.

In another particular embodiment of targeted delivery, the radiopharmaceutical agent can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. See, for example, Emfietzoglou D, Kostarelos K, Sgouros G. An analytical dosimetry study for the use of radionuclide-liposome conjugates in internal radiotherapy. J Nucl Med 2001; 42:499-504, the contents of which are incorporated by reference herein.

In yet another particular embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 November; 57 (5): 749-63, the contents of which are incorporated by reference herein.

In addition to targeted delivery, brachytherapy can be used to deliver the radiopharmaceutical agent to the target site. Brachytherapy is a technique that puts the radiation sources as close as possible to the tumor site. Often the source is inserted directly into the tumor. The radioactive sources can be in the form of wires, seeds or rods. Generally, cesium, iridium or iodine are used.

Systemic radiation therapy is another type of radiation therapy and involves the use of radioactive substances in the blood. Systemic radiation therapy is a form of targeted therapy. In systemic radiation therapy, a patient typically ingests or receives an injection of a radioactive substance, such as radioactive iodine or a radioactive substance bound to a monoclonal antibody.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, *Neptunium*-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95. As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

The physical half-life of the therapeutic radioisotope can be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life could cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such, it is preferred that the radioisotope have high specific activity. The specific activity depends primarily on the production method. Trace metal contaminants can be minimized as they often compete with the radioisotope for the chelator and their metal complexes compete for receptor binding with the radiolabeled chelated agent. The type of radiation that is suitable for use in the methods of the present disclosure can vary. For example, radiation can be electromagnetic or particulate in nature. Electromagnetic radiation useful in the practice of this disclosure includes, but is not limited to, X-rays and gamma rays. Particulate radiation useful in the practice of this disclosure includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this disclosure can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this disclosure.

For tumor therapy, both D and E-particle emitters have been investigated. Alpha particles are particularly good cytotoxic agents because they dissipate a large amount of energy within one or two cell diameters. The E-particle emitters have relatively long penetration range (2-12 mm in the tissue) depending on the energy level. The long-range penetration is particularly important for solid tumors that have heterogeneous blood flow and/or receptor expression. The E-particle emitters yield a more homogeneous dose distribution even when they are heterogeneously distributed within the target tissue.

In a particular embodiment, therapeutically effective amounts of crystalline form ZL or pharmaceutical compositions described herein are administered in combination with a therapeutically effective amount of radiation therapy to treat cancer (e.g., lung cancer, such as non-small cell lung cancer). The amount of radiation necessary can be determined by one of skill in the art based on known doses for a particular type of cancer. See, for example, Cancer Medicine 5$^{th}$ ed., Edited by R. C. Bast et al., July 2000, BC Decker.

Synthetic Methods

Also provided herein are synthetic methods for preparing crystalline form ZL of the compound represented by Structural Formula 1.

In some embodiments, the present disclosure relates to a method of preparing a crystalline form of the compound represented by Structural Formula 1:

(1)

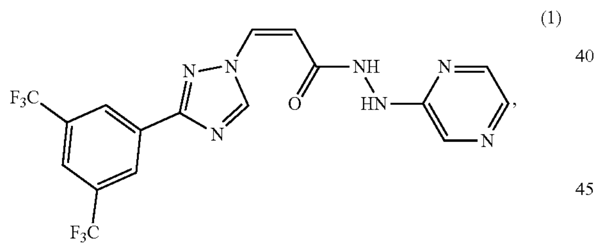

wherein the crystalline form is Form ZL characterized by x-ray powder diffraction peaks at 2θ angles 18.75°, 20.16°, 21.37°, and 23.49°, the method comprising:

combining crystalline Form A of the compound represented by Structural Formula 1 with a solvent, thereby generating a mixture;

thermally cycling the mixture at least once; and isolating the solid particles of crystalline Form ZL, wherein thermally cycling the mixture comprises:

heating the mixture to a first temperature over a first period of time; and cooling the mixture to a second temperature over a second period of time.

Crystalline Form A of the compound represented by Structural Formula 1, employed in the preparation of crystalline Form ZL, is characterized by the following representative XRPD peaks:

| 2Θ, ° | Intensity, % |
|---|---|
| 4.4 | 50.9 |
| 12.4 | 19.9 |
| 13.1 | 23.3 |
| 14.5 | 8.7 |
| 14.7 | 13.1 |
| 15.8 | 23.6 |
| 16.9 | 8.0 |
| 17.5 | 7.9 |
| 18.2 | 22.2 |
| 19.9 | 100.0 |
| 20.3 | 47.0 |
| 21.3 | 85.6 |
| 22.0 | 58.1 |
| 23.1 | 16.2 |
| 23.5 | 43.1 |
| 23.7 | 37.5 |
| 23.9 | 13.6 |
| 25.0 | 44.8 |
| 25.3 | 10.0 |
| 25.6 | 13.6 |
| 27.0 | 21.4 |
| 27.3 | 11.5 |
| 28.3 | 28.6 |
| 28.5 | 31.3 |
| 31.4 | 19.1 |
| 34.8 | 11.3 |
| 37.2 | 13.6 |

Crystalline Form A of the compound represented by Structural Formula 1, employed in the preparation of crystalline Form ZL, is prepared according to the procedure disclosed in U.S. Pat. No. 10,519,139.

In some embodiments, the thermal cycling of the mixture is performed according to the temperature ramp graph in FIG. 4.

In some embodiments of the method of preparing crystalline Form ZL, the thermal cycling is repeated from 2 to 10 times, for example, from 3 to 8 times, such as 5 times. In certain embodiments, the thermal cycling is repeated 2 times, 3 times, 4 times, 5 times, 6 times, 7 times, 8 times, 9 times, or 10 times.

In certain embodiments, the solvent comprises water and alcohol, combined at a certain alcohol-to-water volume ratio.

In certain aspects of the method of preparing crystalline Form ZL, the alcohol-to-water volume ratio is from about 90/10 to about 10/90, for example from about 80/20 to about 20/80, such as from about 70/30 to about 30/70, or from about 60/40 to about 40/60. In certain embodiments, the isopropanol-to-water volume ratio is about 90/10, about 80/20, about 70/30, about 60/40, about 50/50, about 40/60, about 30/70, about 20/80, about 10/90, or about 50/50.

In some embodiments, the alcohol is selected from ethanol, 1-propanol, isopropanol, 1-butanol, or 2-butanol. For example, the alcohol is isopropanol.

In some embodiments of the method of preparing crystalline Form ZL, the first temperature in the range from about 30° C. to about 90° C., such as a temperature in the range from about 35° C. to about 70° C., for example, a temperature in the range from about 40° C. to about 60° C., for example, about 30° C., about 40° C., about 50° C., about 60° C., about 70° C., about 80° C., or about 90° C.

In some embodiments, the first period of time is from about 30 min to about 150 min, for example, from about 60 min to about 120 min. In certain embodiments, the first period of time is about 30 min, about 40 min, about 50 min, about 60 min, about 70 min, about 80 min, about 90 min, about 100 min, about 110 min, about 120 min, about 130 min, about 140 min, or about 150 min.

In some embodiments of the method of preparing crystalline Form ZL, the second temperature is in the range from about −20° C. to about 20° C., for example, from about −10° C. to about 10° C., such as from about −5° C. to about 5° C., or from about 0° C. to about 2° C. In some embodiments, the second temperature is about −20° C., about −15° C., about −10° C., about −5° C., about 0° C., about 5° C., about 10° C., about 15° C., about 20° C., about 25° C., or about 30° C.

In some embodiments, the second period of time is from about 90 min to about 240 min, for example, from about 120 min to about 180 min. In certain embodiments, the second period of time is about 90 min, about 100 min, about 110 min, about 120 min, about 130 min, about 140 min, about 150 min, about 160 min, about 170 min, about 180 min, about 190 min, about 200 min, about 210 min, about 220 min, about 230 min, or about 240 min.

In some embodiments, isolating crystalline Form ZL comprises filtering the mixture, thereby generating a solid and a filtrate, wherein the filtrate comprises solvent components.

In certain embodiments, isolating crystalline Form ZL further comprises drying the solid, thereby obtaining crystalline Form ZL.

In other embodiments, isolating crystalline Form ZL further comprises removing the solvent components of the filtrate, thereby obtaining crystalline Form ZL.

In certain embodiments, the solvents are removed under vacuum. In some embodiments, the temperature of the filtrate during the solvent removal is maintained at a third temperature. In some embodiments, the third temperature is the range from about 20° C. to about 80° C., for example, 30° C. to about 70° C., such as a temperature in the range from about 40° C. to about 60° C., for example, about 50° C. In certain embodiments, the temperature of the filtrate during the solvent removal is maintained at about 20° C., about 30° C., about 40° C., about 50° C., about 60° C., about 70° C., or about 80° C.

In one embodiment, the disclosure relates to a method of preparing crystal Form ZL of the compound represented by Structural Formula (I), the method comprising:

(a) combining crystal Form A of the compound represented by Structural Formula (I) and a solvent comprising isopropanol and water, thereby forming a mixture;
(b) heating the mixture while stirring for a first period of time and at a first temperature;
(c) cooling the mixture while stirring for a second period of time and at a second temperature;
(d) filtering the mixture, thereby forming a filtrate;
(e) removing solvents from the filtrate; and
(f) isolating crystal Form ZL.

In another embodiment, the disclosure relates to a method of preparing crystal Form ZL of the compound represented by Structural Formula (I), the method comprising:

(a) combining crystal Form A of the compound represented by Structural Formula (I) and a solvent comprising isopropanol and water, thereby forming a mixture;
(b) heating the mixture while stirring at a first temperature until crystalline Form A is dissolved;
(c) cooling the mixture for a second period of time and to a second temperature, thereby forming a final suspension;
(d) filtering the final suspension; and
(f) isolating crystal Form ZL.

“Solvent,” as used herein, refers to a single solvent or a mixture of two or more (typically, two) different solvents. Exemplary solvents include water and organic solvents such as, but not limited to, methanol, ethanol, diisopropyl ether, isopropanol, ethyl acetate, and isopropyl acetate.

“Alcohol,” as used herein, refers to an organic compound in which the hydroxyl functional group is bound to a carbon. Exemplary alcohols include, but are not limited to methanol, ethanol, 1-propanol, isopropanol, 1-butanol, 2-butanol, neopentyl alcohol, isooctanol, isoamyl alcohol, cyclohexanol, methyl cyclohexanol, ethylene glycol, and diethylene glycol.

In some embodiments, isolating the solid particles of crystalline Form ZL is effected by filtration and, optionally, rinsing of the filtered solids with a solvent (e.g., a chilled solvent), although other means of isolating the solid particles are known in the art. Other means of isolating the solid particles of crystalline Form ZL include, but are not limited to, distilling liquid away from the solid particles or otherwise drying the solid particles, for example, by heating, by subjecting to reduced pressure (e.g., in vacuo) or any combination of the foregoing.

“Room temperature” and “ambient temperature,” as used herein, means a temperature of from about 16° C. to about 25° C.

“Ambient conditions,” as used herein, refers to room temperature and atmospheric pressure conditions.

Drying crystalline Form ZL of the compound represented by Structural Formula 1 can be accomplished, for example, by distilling any liquid present away from the solid crystalline form(s), by exposing the solid crystalline form(s) to ambient conditions or passing a stream of gas, such as nitrogen gas, over the solid crystalline form(s) (and thereby inducing the evaporation or desolvation of any liquid or entrapped volatile substance), by subjecting the solid crystalline form(s) to reduced pressure (e.g., in vacuo) or any combination of the foregoing.

It is understood that, quite often, in practice, the steps for preparing crystalline Form ZL according to the methods described herein entail a combination of heating, maturing and/or drying.

EXEMPLIFICATION

General Materials and Methods

As used herein, compound of Structural Formula 1 is the compound represented by structural Formula 1.

XRPD

Per USP guidelines, variable hydrates and solvates may display peak variances greater than 0.2° 2θ and therefore peak variances of 0.2° 2θ are not applicable to these materials.

“Prominent Peaks” are a subset of the entire observed peak list. Prominent peaks are selected from observed peaks by identifying preferably non-overlapping, low-angle peaks, with strong intensity.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks." In general, the more data collected to determine Representative Peaks, the more confident one can be of the classification of those peaks.

"Characteristic peaks," to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° 2θ. Not all crystalline polymorphs of a compound necessarily have at least one characteristic peak.

Solid samples were ground with a mortar and pestle to provide a powder prior to the collection of XRPD data. In some instances, see for example FIG. 8 and FIG. 9, sample was not ground prior to the collection of XRPD data.

XRPD diffractograms were collected in transmission geometry on a PANalytical Empyrean diffractometer using Cu Ka radiation (45 kV, 40 mA). A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The software used for data collection was X'Pert Data Collector using X'Pert Operator Interface. The data were analyzed and presented using Diffrac Plus EVA or HighScore Plus. Samples were prepared and analyzed in a metal 96 well-plate in transmission mode. X-ray transparent film was used between the metal well-plate. Solids were placed on this film (approximately 1-2 mg) for scanning.

The details of the standard screening data collection method are:

Angular range: 2.5 to 32.0° 2θ;

Step size: 0.0130° 2θ;

Collection time: 12.75 s/step (total collection time of 2.07 min).

XRPD diffractograms were collected in reflection geometry on a Bruker D2 Phaser diffractometer using Cu Ka radiation (30 kV, 10 mA) at a step size of 0.01° per 10.66 s. A 1 mm divergence slit was used on the incident beam. A 1D CCD (SSD 160) detector, placed on the diffracted beam, was fitted with a 2.5 μm Ni foil (Kb) filter and 2.5° receiving Soller Slit. The data were analyzed and presented using Diffrac Plus EVA. Samples were prepared and analyzed in an air sensitive sample holder with zero background insert. The sample was covered with 3015 Mylar® Pre-Cut Circular Window Film (0.25 Mil (6μ) thick, 2.5" (64 mm) diameter) and rotated at 15 rpm.

TGA

TGA data were collected on a TA Instruments Q500 TGA, equipped with a 16 position auto-sampler. Typically, 5-10 mg of each sample was loaded onto a pre-tared aluminum DSC pan and heated to 10° C./min from ambient temperature to 350° C. A nitrogen purge at 60 ml/min was maintained over the sample. The instrument control software was Advantage for Q Series and Thermal Advantage and the data were analysed using Universal Analysis or TRIOS

DSC

DSC data were collected on a TA Instruments Q2000 equipped with a 50 position auto-sampler. Typically, 0.5-3 mg of each sample, in a pin-holed aluminium pan, was heated at 10° C./min from 25° C. to 250° C. A purge of dry nitrogen at 50 ml/min was maintained over the sample. Modulated temperature DSC was carried out using an underlying heating rate of 2° C./min and temperature modulation parameters of ±0.318° C. (amplitude) every 60 seconds (period). The instrument control software was Advantage for Q Series and Thermal Advantage and the data were analysed using Universal Analysis or TRIOS.

DVS

Sorption isotherms were obtained using a SMS DVS Intrinsic moisture sorption analyser, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy±0.005 mg). Typically, 5 to 30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

TABLE 1

Method for SMS DVS Intrinsic experiments

| Parameter | Value |
|---|---|
| Adsorption - Scan 1 | 40-90 |
| Desorption, Adsorption - Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

The sample was recovered after completion of the isotherm and re-analysed by XRPD.

Example 1—Preparation of Crystalline Form ZL

Method A. Crystalline Form A of the compound represented by Structural Formula 1 (150 g) was suspended in 900 mL of mixture of isopropanol and water (1:1 v/v ratio of isopropanol to water) in a 1000 mL cylindrical jacketed vessel with an overhead stirrer. The temperature ramp depicted in FIG. 4 was executed for 5 cycles. The resulting suspension was filtered through filter paper. The filtrate was subjected to reduced pressure while the temperature of the filtrate was maintained at 50° C. until the solvents were removed and a dry crystalline Form ZL of the compound represented by Structural Formula 1 was obtained.

Method B. Crystalline Form A of the compound represented by Structural Formula 1 (83.56 g) was suspended in 492 mL of isopropanol/water mixture (70:30 v/v ratio of isopropanol to water), heated to 50° C., and stirred until all the solids dissolved. A 5 mL aliquot of the solution was taken into a 20 mL vial, which was immediately immersed in ice water. Once a thick suspension had formed, the solids were filtered to provide crystalline Form ZL of the compound represented by Structural Formula 1.

In some embodiments, crystalline form ZL of the compound represented by Structural Formula 1 can be prepared by Method A or Method B. The XRPD pattern of Form ZL is depicted in FIG. 1, and the peaks are tabulated in Table 2. The XRPD analysis was conducted on ground material using transmittance mode.

TABLE 2

| Angle 2Θ ° | Intensity % |
|---|---|
| 11.28 | 13.40 |
| 12.91 | 10.50 |
| 13.50 | 25.10 |
| 14.00 | 56.70 |
| 15.89 | 34.90 |
| 16.77 | 49.50 |
| 17.21 | 24.40 |
| 18.75 | 69.60 |
| 20.16 | 100.00 |
| 20.72 | 43.10 |
| 20.98 | 33.30 |
| 21.37 | 91.90 |
| 22.55 | 50.20 |
| 22.96 | 32.80 |
| 23.49 | 70.60 |
| 24.16 | 56.90 |
| 25.02 | 10.50 |
| 26.08 | 21.80 |
| 26.93 | 23.20 |
| 27.21 | 53.20 |
| 27.62 | 16.00 |
| 28.25 | 22.00 |
| 28.99 | 42.40 |
| 29.95 | 14.20 |

The TGA trace of crystalline Form ZL is depicted in FIG. 2. No weight change is observed from ambient temperature to about 200° C., followed by sample degradation.

The DSC trace of crystalline Form ZL is depicted in FIG. 3. The DSC thermogram displays a sharp endothermic peak observed at approximately 184° C., which corresponds to melting.

Lack of weight change observed upon heating of Form ZL to 200° C., as well as absence of phase transitions and relatively high melting point demonstrated in the DSC experiment indicate favorable thermodynamic stability of Form ZL for pharmaceutical applications. Specifically, it is likely to be robust under heating due to compression forces of tablet manufacturing, and it is likely to have good thermal stability in tablet form, leading to long product shelflife.

Figure 5:
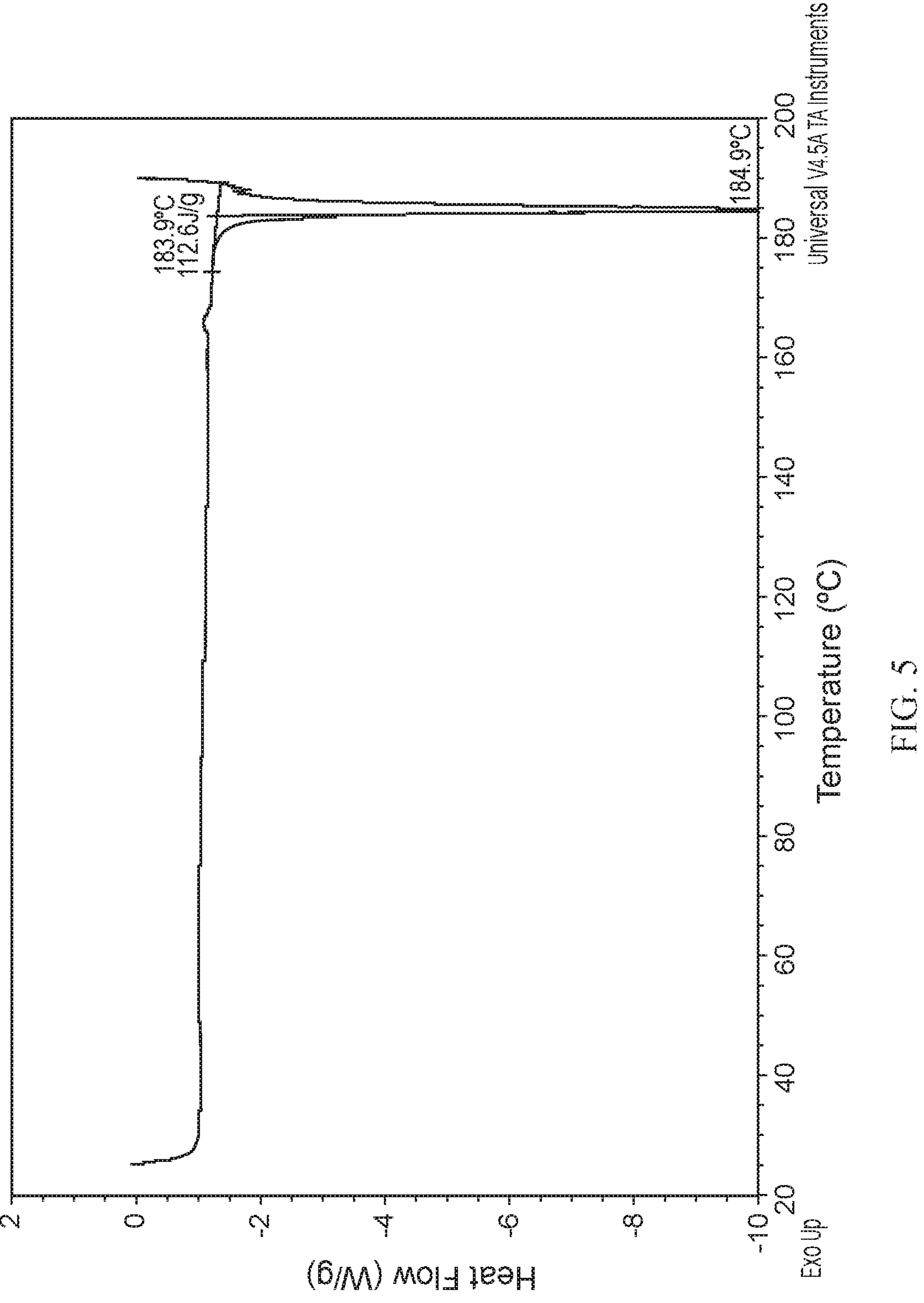
FIG. 5 is a graph depicting a DSC thermogram of the crystalline Form ZL of the compound represented by Structural Formula 1, performed at 10° C./min.
Figure 6:
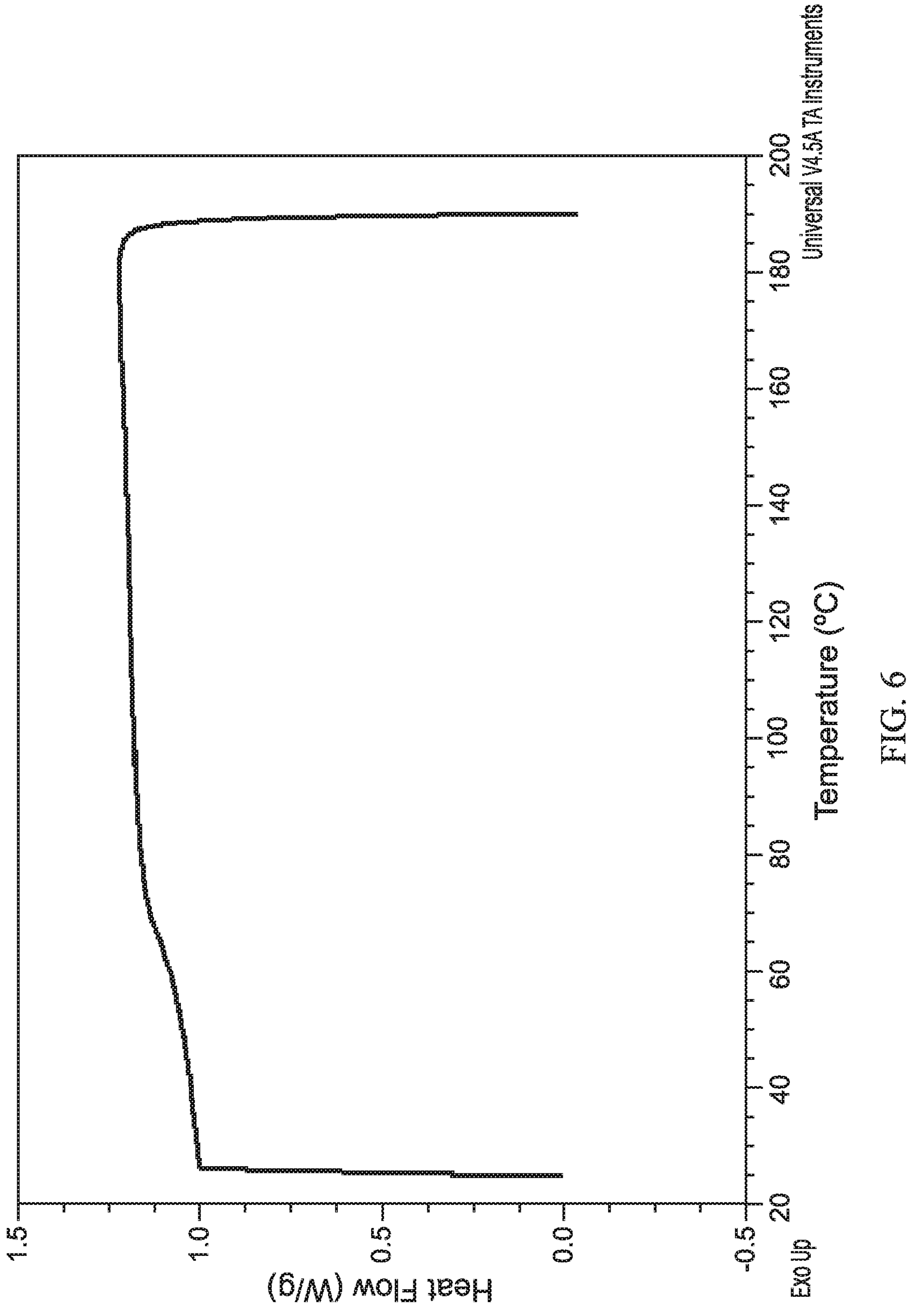
FIG. 6 is a graph depicting a DSC thermogram corresponding to the cooling of the material obtained after melting of the crystalline Form ZL of the compound represented by Structural Formula 1.
Figure 7:
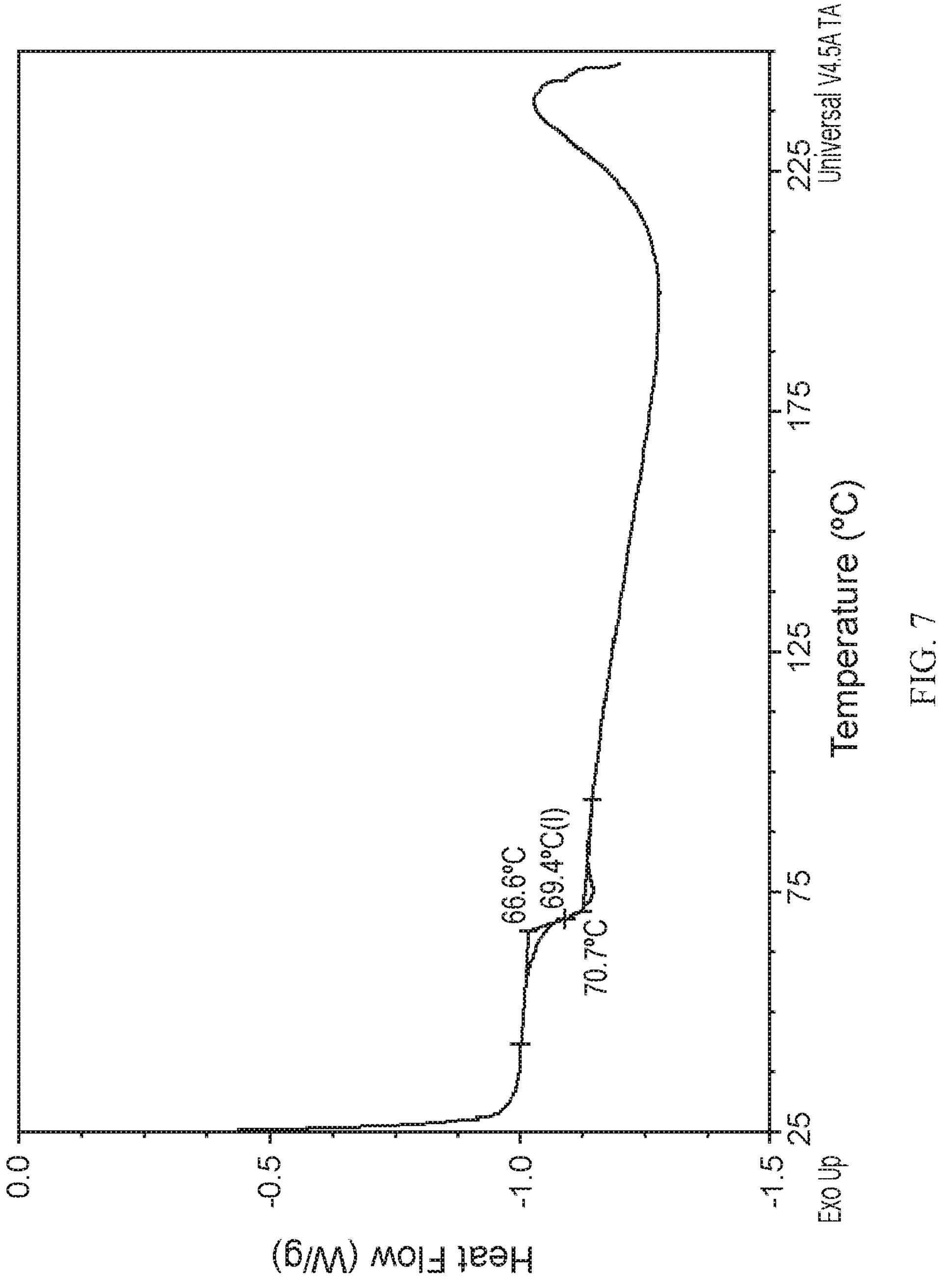
FIG. 7 is a graph depicting a DSC thermogram corresponding to the heating of the material obtained after melting of the crystalline Form ZL of the compound represented by Structural Formula 1.

Additional DSC study was performed under the following conditions:

(a) heating crystalline Form ZL to 190° C. at 10° C./min to melt the crystals (the corresponding DSC thermogram is shown in FIG. 5);

(b) cooling the resulting material to 25° C. at 10° C./min (the corresponding DSC thermogram is shown in FIG. 6); and (c) heating the material again to 250° C. at 10° C./min (the corresponding DSC thermogram is shown in FIG. 7).

The DSC thermogram in FIG. 7 shows the material obtained after the initial melting event in step (a) was amorphous, with a glass transition temperature (Tg) at 69.4° C. and no melting event before degradation onset at ~200° C.

The DVS pattern of crystalline Form ZL is depicted in FIG. 4. Two DVS cycles have been recorded. The DVS pattern displays a weight gain of about 0.16% at 90% RH and gradual reversible uptake over 0-90% RH range. The minimal and reversible moisture uptake demonstrated by crystalline Form ZL is a physical property desirable in crystalline forms utilized in pharmaceutical compositions. XRPD pattern of Form ZL after the DVS cycle is identical to the XRPD of the Form ZL prior to the DVS cycle.

Example 2—XRPD of Crystalline Form ZL

Crystalline Form ZL can be obtained by Methods A and B and may be isolated in the form of plate-like crystals. When XRPD analysis is directly conducted on the plate-like crystals, rather than on a ground test sample, XRPD diffractograms (in reflectance or transmittance modes) distinct from that depicted in FIG. 1 (ground test sample/transmittance mode) are obtained. This distinct XRPD pattern obtained in reflectance mode is depicted in FIG. 8 and the peaks are tabulated in Table 3; while the distinct XRPD pattern obtained in transmittance mode is shown in FIG. 9 and the peaks are tabulated in Table 4. The alternate XRPD patterns depicted in FIGS. 8 and 9 for the unground plate-like crystals are a result of an analytical artifact and the XRPD patterns of FIG. 1 and FIGS. 8 and 9 are all crystalline Form ZL as described and prepared herein.

TABLE 3

| Angle 2Θ ° |
|---|
| 8.33 |
| 12.61 |
| 15.23 |
| 16.90 |
| 16.62 |
| 17.28 |
| 19.97 |
| 21.26 |
| 21.63 |
| 26.13 |
| 30.10 |
| 34.58 |
| 39.10 |
| 43.72 |
| 53.13 |

TABLE 4

| Angle 2Θ ° | Intensity % |
|---|---|
| 13.5 | 21.9 |
| 14.0 | 27.8 |
| 15.9 | 7.4 |
| 16.8 | 61.6 |
| 18.8 | 19.6 |
| 19.8 | 13.6 |
| 20.1 | 47.4 |
| 20.7 | 21.6 |
| 20.9 | 27.3 |
| 21.4 | 100.0 |
| 22.5 | 33.0 |
| 23.0 | 27.0 |
| 23.5 | 20.7 |
| 24.2 | 21.0 |
| 26.1 | 8.5 |
| 26.9 | 30.7 |
| 27.2 | 60.2 |
| 27.7 | 9.9 |
| 28.2 | 9.7 |
| 29.0 | 15.9 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A crystalline form of the compound represented by Structural Formula 1:

(1)

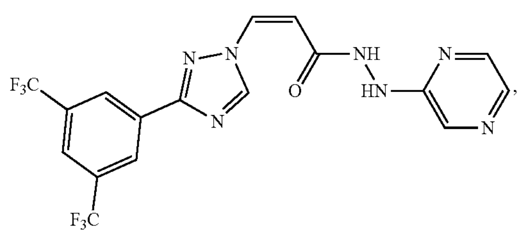

wherein (i) the crystalline form is characterized by x-ray powder diffraction peaks at 2θ angles 18.75°, 20.16°, 21.37°, and 23.49° in an x-ray powder diffractogram obtained in a transmittance mode with a ground sample of the crystalline form;

(ii) the crystalline form is characterized by x-ray powder diffraction peaks at 2θ angles 12.61°, 16.90°, 21.26°, and 34.58° in an x-ray powder diffractogram obtained in a reflectance mode with an unground sample of the crystalline form; or (iii) the crystalline form is characterized by x-ray powder diffraction peaks at 2θ angles 16.8°, 20.1°, 21.4°, and 27.2° in an x-ray powder diffractogram obtained in a transmittance mode with an unground sample of the crystalline form.

2. The crystalline form of claim 1, wherein the crystalline form is characterized by x-ray powder diffraction peaks at 2θ angles 18.75°, 20.16°, 21.37°, 23.49°, and 24.16° obtained in accordance with (i).

3. The crystalline form of claim 1, wherein the crystalline form is characterized by x-ray powder diffraction peaks at 2θ angles 14.00°, 18.75°, 20.16°, 21.37°, 22.55°, 23.49°, 24.16°, and 27.21° obtained in accordance with (i).

4. The crystalline form of claim 1, wherein the crystalline form is characterized by x-ray powder diffraction peaks at 2θ angles of 14.00°, 15.89°, 16.77°, 18.75°, 20.16°, 20.72°, 20.98°, 21.37°, 22.55°, 22.96°, 23.49°, 24.16°, 27.21°, and 28.99° obtained in accordance with (i).

5. The crystalline form of claim 1, wherein the crystalline form is characterized by an x-ray powder diffraction pattern substantially in accordance with that depicted in FIG. 1 or FIG. 9.

6. The crystalline form of claim 1, wherein the crystalline form is characterized by a DSC thermogram having an endothermic event at about 184° C.

7. The crystalline form of claim 1, wherein the crystalline form is characterized by a DSC thermogram substantially in accordance with that depicted in FIG. 5.

8. The crystalline form of claim 1, wherein the crystalline form is characterized by x-ray powder diffraction peaks at 2θ angles 8.33°, 12.61°, 15.23°, 16.62°, 16.90°, 17.28°, 19.97°, 21.26°, 21.63°, 30.10°, 34.58°, 39.10°, 43.57°, and 53.13° obtained in accordance with (ii).

9. The crystalline form of claim 1, wherein the crystalline form is characterized by x-ray powder diffraction peaks at 2θ angles 13.5°, 14.0°, 16.8°, 20.1°, 20.7°, 20.9°, 21.4°, 22.5°, 23.0°, 23.5°, 24.2°, 26.9°, and 27.2° obtained in accordance with (iii).

10. The crystalline form of claim 1, wherein the crystalline form is characterized by an x-ray powder diffraction pattern substantially in accordance with that depicted in FIG. 8.

11. A tablet, comprising the crystalline form of claim 1 and a pharmaceutically acceptable carrier.

12. A method of preparing a crystalline form of the compound represented by Structural Formula 1:

(1)

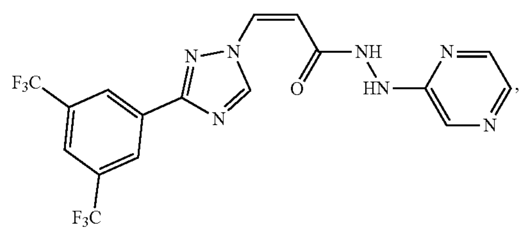

wherein the crystalline form is characterized by x-ray powder diffraction peaks at 2θ angles 18.75°, 20.16°, 21.37°, and 23.49° in an x-ray powder diffractogram obtained in a transmittance mode with a ground sample of the crystalline form, the method comprising:

combining crystalline Form A of the compound represented by Structural Formula 1 with a solvent, thereby generating a mixture;

thermally cycling the mixture at least once; and isolating the solid particles of the crystalline form, wherein thermally cycling the mixture comprises:

heating the mixture to a first temperature over a first period of time; and cooling the mixture to a second temperature over a second period of time.

13. The method of claim 12, wherein the solvent comprises water and alcohol, and the solvent has an alcohol-to-water volume ratio from about 90/10 to about 10/90.

14. The method of claim 13, wherein the alcohol is selected from ethanol, 1-propanol, isopropanol, 1-butanol, or 2-butanol.

15. The method of claim 12, wherein the first temperature is from about 30° C. to about 90° C.

16. The method of claim 12, wherein the first period of time is from about 30 minutes to about 150 minutes.

17. The method of claim 12, wherein the second temperature is from about −20° C. to about 20° C.

18. The method of claim 12, wherein the second period of time is from about 90 minutes to about 240 minutes.

19. The method of claim 12, wherein the mixture is thermally cycled from 2 times to 10 times.

20. A method for treating or preventing a CRM1-associated disease or disorder, the method comprising administering to a subject in need thereof a therapeutically or prophylactically effective amount of the crystalline form of claim 1.

21. The method of claim 20, wherein the disorder is a proliferative disorder, cancer, an inflammatory disorder, an autoimmune disorder, a viral infection, an ophthalmological disorder, a neurodegenerative disorder, a disorder of abnormal tissue growth, a disorder related to food intake, an allergic disorder, or a respiratory disorder.

22. The method of claim 21, wherein the disorder is cancer.

23. The method of claim 21, wherein the cancer is multiple myeloma.

* * * * *